United States Patent
Hashizume et al.

(10) Patent No.: US 9,498,154 B2
(45) Date of Patent: Nov. 22, 2016

(54) MEASURING SYSTEM CAPABLE OF SEPARATING LIQUID AND DETERMINING BOUNDARY OF SEPARATED LIQUID

(75) Inventors: Nobuya Hashizume, Kyotanabe (JP); Keishi Kitamura, Kyoto (JP); Takahiro Nishimoto, Kyoto-fu (JP); Tomoaki Tsuda, Kyoto (JP); Yuichi Kimura, Narita (JP); Chie Seki, Kamakura (JP); Iwao Kanno, Chiba (JP)

(73) Assignees: SHIMADZU CORPORATION, Kyoto (JP); NATIONAL INSTITUTES FOR QUANTUM AND RADIOLOGICAL SCIENCE AND TECHNOLOGY, Chiba (JP)

( * ) Notice: Subject to any disclaimer, the term of this patent is extended or adjusted under 35 U.S.C. 154(b) by 702 days.

(21) Appl. No.: 13/636,946

(22) PCT Filed: Dec. 28, 2010

(86) PCT No.: PCT/JP2010/007602
§ 371 (c)(1),
(2), (4) Date: Sep. 24, 2012

(87) PCT Pub. No.: WO2011/117952
PCT Pub. Date: Sep. 29, 2011

(65) Prior Publication Data
US 2013/0010108 A1  Jan. 10, 2013

(30) Foreign Application Priority Data
Mar. 24, 2010 (JP) ................. 2010-068151

(51) Int. Cl.
*A61B 5/153* (2006.01)
*A61B 5/155* (2006.01)
(Continued)

(52) U.S. Cl.
CPC ......... *A61B 5/1427* (2013.01); *A61B 5/15003* (2013.01); *A61B 5/155* (2013.01);
(Continued)

(58) Field of Classification Search
CPC ......... G06K 9/00; H04N 7/18; A61B 5/1427
USPC ........................................... 348/142
See application file for complete search history.

(56) References Cited

U.S. PATENT DOCUMENTS 6,125,213 A    9/2000  Morimoto
7,231,243 B2 *  6/2007  Tearney ............. A61B 1/00082
                                              600/407
(Continued)

FOREIGN PATENT DOCUMENTS

EP    2551664 A1    1/2013
JP    10-232915 A   9/1998
(Continued)

OTHER PUBLICATIONS

Opelt et al., A Boundary-Fragment+model for object detection, 2006, LNCS: 3952, pp. 575-588.*

(Continued)

*Primary Examiner* — Jay Patel
*Assistant Examiner* — Irfan Habib
(74) *Attorney, Agent, or Firm* — McDermott Will & Emery LLP

(57) ABSTRACT

A boundary calculating unit is provided for determining boundaries between separated plasma and blood cell or air and plasma whose image is picked up by an image pickup unit. With such boundary calculating unit provided, the boundaries between the separated plasma and blood cell or air and plasma can be determined, and areas of the separated air, plasma, and blood cell can be determined accurately. Particularly, a straight line drawing unit is provided for drawing, on the image picked up, a plurality of straight lines parallel to grooves in a disk which performs plasma separation. The boundary calculating unit can easily determine the boundaries by determining the boundaries based on a profile of the plurality of straight lines drawn by the straight line drawing unit.

10 Claims, 11 Drawing Sheets

(51) Int. Cl.
*A61B 5/157* (2006.01)
*G01N 15/04* (2006.01)
*G01N 15/05* (2006.01)
*G01N 33/49* (2006.01)
*G01N 21/07* (2006.01)
*G01N 21/64* (2006.01)
*A61B 5/15* (2006.01)

(52) U.S. Cl.
CPC ........ *A61B 5/157* (2013.01); *A61B 5/150213* (2013.01); *A61B 5/150221* (2013.01); *A61B 5/150755* (2013.01); *G01N 15/042* (2013.01); *G01N 15/05* (2013.01); *G01N 21/07* (2013.01); *G01N 21/6428* (2013.01); *G01N 33/491* (2013.01); *A61B 5/153* (2013.01); *G01N 2015/045* (2013.01)

(56) References Cited

U.S. PATENT DOCUMENTS

| | | | | |
|---|---|---|---|---|
| 8,538,163 | B2* | 9/2013 | Moesle | G06T 7/0085 382/199 |
| 8,965,132 | B2* | 2/2015 | Poyil | G06T 7/0085 382/199 |
| 2006/0044359 | A1* | 3/2006 | Sugahara | B41J 2/14233 347/68 |
| 2008/0063236 | A1* | 3/2008 | Ikenoue | G06K 9/32 382/103 |
| 2009/0208071 | A1* | 8/2009 | Nishimura | A61B 1/041 382/128 |
| 2009/0232486 | A1* | 9/2009 | Sato | G01N 21/6452 396/200 |
| 2010/0294950 | A1* | 11/2010 | Kitamura | A61B 5/1427 250/458.1 |
| 2011/0081087 | A1* | 4/2011 | Moore | G06K 9/00711 382/199 |

FOREIGN PATENT DOCUMENTS

| | | |
|---|---|---|
| JP | 2004-361384 A | 12/2004 |
| JP | 2006-145484 A | 6/2006 |
| JP | 2007-271507 A | 10/2007 |
| WO | WO-2007/044938 | 4/2007 |
| WO | WO-2009/093306 | 7/2009 |

OTHER PUBLICATIONS

L. Convert et al., "A Microvolumetric β Blood Counter for Pharmacokinetic PET Studies in Small Animals," IEEE Transactions on Nuclear Science, vol. 54, No. 1, Feb. 2007.

H.-M. Wu et al., "In Vivo Quantitation of Glucose Metabolism in Mice Using Small-Animal PET and a Microfluidic Device," Nov. 16, 2006; Revision accepted Jan. 23, 2007, pp. 837-845.

HM Wu et al., "Performing Longitudinal Measurements in Rodents Using Small Animal PET Imaging," Conf. Rec. IEEE NSS & MIC, M10-398, 2008.

H. Toyama et al., "Evaluation of anesthesia effects on [$^{18}$F]FDG uptake in mouse brain and heart using small animal PET," Nuclear Medicine and Biology 31 (2004) 251-256.

International Search Report issued in International Patent Application No. PCT/JP2010/007602 dated Mar. 29, 2011.

Extended European Search Report issued in European Application No. 10848345.4 dated Jun. 12, 2013.

* cited by examiner

MEASURING SYSTEM CAPABLE OF SEPARATING LIQUID AND DETERMINING BOUNDARY OF SEPARATED LIQUID

RELATED APPLICATIONS

This application is the U.S. National Stage application under 35 U.S.C. §371 of International Application No. PCT/JP2010/007602, filed on Dec. 28, 2010, which was published as WO 2011/117952 on Sep. 29, 2011. The application is incorporated herein by reference.

TECHNICAL FIELD

This invention relates to a measuring system for measuring light generated from a luminescent or fluorescent substance included in a liquid to be measured, or radiation included in the liquid to be measured.

BACKGROUND ART

The measuring system is used in a liquid collecting apparatus, for example. The liquid collecting apparatus will be described taking a blood collecting apparatus which collects blood, for example. The blood collecting apparatus is used for quantitative analysis in nuclear medicine diagnosis (e.g. PET (Positron Emission Tomography), SPECT (Single Photon Emission CT) and so on), and are used especially for measurement of a radioactive concentration in arterial blood of small animals (e.g. mice, rats and so on). Conventionally, the following modes (a)-(d) are employed in the above quantitative analysis of small animals:

(a) Manual Blood Collection

Blood delivering itself under blood pressure from the other end of a catheter inserted into a mouse artery is received in a suitable receptacle. Then, a fixed volume of the blood in the receptacle is sucked up with a volumetric pipette, and a radioactive concentration in the whole blood is measured by calculating (i.e. counting) radiation in the sucked-up blood. Further, plasma is obtained by centrifugal separation of the blood remaining in the receptacle, which is similarly collected with a volumetric pipette to measure a radioactive concentration in plasma.

(b) Artery Channel β-Ray Detector

A β$^+$ ray detector is installed in an arterial blood channel to measure a radioactive concentration in blood. β$^+$ rays are detected with a plastic scintillator or PIN diode. In Nonpatent Document 1, for example, a diode has a long and thin shape with a length of 30 [mm], and a detectable area is increased by installing a tube containing blood along the direction of a long side, thereby to secure detection efficiency.

(c) Microfluidic Device Mode

This is a mode which, as shown in FIG. 15, leads arterial blood delivering itself under mouse blood pressure onto a microchip (device) MC. The microchip MC has, arranged thereon, one main flow path $F_M$, selectable branch flow paths $F_B$, and side flow paths $F_N$ for feeding a mixed liquid H of heparin solution and physiological saline used for flow path cleaning or blood discharging, and for draining used mixed liquid H of heparin solution and physiological saline and blood B. A receptacle is placed at the end of each branch flow path $F_B$, and one of the branch flow paths $F_B$ is selected by a gas pressure of argon gas Gas supplied to the microchip MC or a mechanism of the microchip MC. With one of the branch flow paths $F_B$ selected, blood B is poured in. The flow velocity of the blood B and the mixed liquid H of heparin solution and physiological saline is increased by placing the interior of each branch flow path of the microchip MC at negative pressure, and further installing a peristaltic pump. Each of the flow paths $F_M$ and $F_B$ is formed by grooving the microchip MC in a predetermined size. It is the characteristic of the microchip MC that a minute volume of blood B is specified if a groove length or a groove area of the poured-in blood B is known. With the blood B of a predetermined volume filling the flow paths, based on the specified minute volume, the blood B is sent along with the mixed liquid H of heparin solution and physiological saline into a predetermined receptacle (not shown) by feeding the mixed liquid H of heparin solution and physiological saline under pressure. Subsequently, each of the flow paths $F_M$ and $F_B$ is cleaned with the mixed liquid H of heparin solution and physiological saline to be ready for a next blood collection. The blood B in the receptacle is washed out along with the physiological saline into another receptacle, and the radiation in the blood B is counted with a well counter (see Nonpatent Documents 2 and 3, and Patent Document 1, for example).

(d) Radioactivity Time Variation Measurement from PET Images

This is a technique which sets an area of interest to the left ventricle of PET dynamic images acquired, and determining time variations of radioactive concentration in the area (see Nonpatent Document 4, for example).

However, when the above techniques are applied to radioactivity measurement in arterial blood of small animals, there arise the following problems.

(a) Manual Blood Collection

In the case of manual blood collection, it is possible to determine accurately a radioactive concentration in the whole blood from the blood obtained, and also a radioactive concentration in plasma from the plasma resulting from centrifugal separation. However, the question of the operator's procedure imposes restrictions to blood collecting intervals, and it is impossible to acquire data of rapid variations (in the order of several seconds) in the radioactive concentration occurring immediately after medication. Further, since a large amount of blood is collected at a time, the number of times of blood collection is limited in order to avoid the small animals dying from loss of blood.

(b) Artery Channel β-Ray Detector

It is possible to track minute time variations in the radioactive concentration in the whole blood through the tube by which arterial blood flows through the β$^+$ ray detector. However, it is impossible to acquire a radioactive concentration in plasma which serves as the input function for quantitative analysis model.

(c) Microfluidic Device Mode

This mode can track minute time variations in the radioactive concentration in a slight amount of blood. Although data of collected blood is washed out to a separate receptacle, there is no function to put it to centrifugal separation to acquire a radioactive concentration in plasma which serves as the input function for quantitative analysis model.

(d) Radioactivity Time Variation Measurement from PET Images

This mode can obtain only time variations in whole blood radioactive concentration. Further, in the operation to set the area of interest to the left ventricle, quantification of the radioactive concentration obtained from the left ventricle is impaired due to a partial volume effect from tissues surrounding the left ventricle. There are also problems that specifying the left ventricle is not easy particularly with a small individual such as a mouse, and that it is also difficult, with medication inducing a high degree of accumulation in tissues around the heart, to set the area of interest to the left ventricle without anatomical information.

So, in order to solve these problems, there is provided a flow path through which a liquid (e.g. blood) to be measured flows, with an extracting device provided in an intermediate position of the flow path to insert a gas or a liquid other than the liquid to be measured, as separators, at designated predetermined intervals, thereby to take out the liquid to be measured, as separated in the time series (see Patent Document 2, for example). In this Patent Document 2, the liquid can be taken out in minute volumes of about 1 [µL], for example, by inserting the separators consisting of the gas or liquid while continuously feeding the liquid to be measured into the flow path. And consumption of the liquid to be measured accompanying a cleaning liquid (heparin solution in the case of blood collection) for every collection as in the prior art can be held down, and the amount of collected liquid can be minimized. Since the operation to insert the separators is excellent in speed, repeated collection in a short time, i.e. frequency of collection, can be secured. As a result, the amount of collected liquid can be reduced, and the frequency of collection can be secured. Where the liquid to be measured is blood, the amount of collected blood can be reduced, and the frequency of blood collection can be secured.

Further, where the liquid to be measured is blood, the blood is put to centrifugal separation, and the radiation included in plasma and blood cell resulting from plasma separation is separately counted. Therefore, the radioactive concentration in plasma can be measured.

PRIOR ART DOCUMENTS

Patent Documents

[Patent Document 1]
International publication WO2007-044938
[Patent Document 2]
International publication WO2009-093306

Nonpatent Documents

[Nonpatent Document 1]
L. Convert, G. M. Brassard, J. Cadorette, D. Rouleau, E. Croteau, M. Archambault, R. Fontaine, and R. Lecomte, "A microvolumetric β blood counter for pharmacokinetic PET studies in small animals," IEEE Nuclear Sci, vol. 54, no. 1, 2007.
[Nonpatent Document 2]
H.-M. Wu, G. Sui, C.-C. Lee, M. L. Prins, W. Ladno, H.-D. Lin, A. S. Yu, M. E. Phelps, and S.-C. Huang, "In vivo quantitation of glucose metabolism in mice using small-animal PET and a microfluidic device," J Nucl Med, vol. 48, pp. 837-845, 2007.
[Nonpatent Document 3]
H.-M. Wu, R. W. Silverman, N. G. Harris, and R. L. Sutton, "Performing Longitudinal Measurements in Rodents Using Small Animal PET Imaging", Conf Rec IEEE NSS & MIC, M10-398, 2008.
[Nonpatent Document 4]
Hiroshi Toyama, Masanori Ichise, Jeih-San Liow, Douglass C. Vines, Nicholas M. Seneca, Kendra J. Modell, Jurgen Seidel, Michael V. Green, Robert B. Innis, "Evaluation of anesthesia effects on [$^{18}$F] FDG uptake in mouse brain and heart using small animal PET", Nuclear Medicine and Biology, 31, 251-256, 2004.

DISCLOSURE OF THE INVENTION

Problem to be Solved by the Invention

However, Patent Document 2 with such construction has the following drawback.

For separating plasma and blood cell, a volume of each is determined based on image shading differences, to determine a radioactive concentration in blood of $\beta^+$ rays per unit volume. However, there is a problem that actual shading differences are not uniform. Therefore, actual boundaries between plasma and blood cell are not known. Unless actual boundaries are known, the radioactive concentration of $\beta^+$ rays cannot be determined accurately.

This invention has been made having regard to the state of the art noted above, and its object is to provide a measuring system which allows boundaries of a separated liquid to be determined, and which allows for an accurate determination of areas of the separated liquid.

Means for Solving the Problem

To fulfill the above object, this invention provides the following construction.

A measuring system according to this invention is a measuring system for measuring light generated from a luminescent or fluorescent substance included in a liquid to be measured, or radiation included in the liquid to be measured, comprising a separating device for separating the liquid to be measured, an image pickup device for picking up an image of the liquid separated by the separating device, and a boundary calculating device for determining boundaries of the separated liquid picked up by the image pickup device, wherein the measuring system measures the light or the radiation in areas of the liquid divided by the boundary calculating device, respectively;
  the separating device is a flat plate grooved in a predetermined size;
  an edge enhancing device is provided for enhancing, as edges, the shading differences in the image of the separated liquid in the flat plate picked up by the image pickup device;
  a flow path position extracting device is provided for extracting, based on design information on grooves having the predetermined size in the flat plate, and the flat plate, flow path positions of the grooves by adjusting pixel positions of the grooves in the image with the edges enhanced by the edge enhancing device; and the boundary calculating device determines the boundaries based on the image in the pixel positions adjusted by the flow path position extracting device.

Functions and Effects

When an attempt is made to determine separating locations of the liquid based only on shading differences of the image, there is a problem that the boundaries of the separated liquid cannot be extracted accurately if the shading differences are not uniform. Particularly where the liquid is blood, plasma, because it is clear and colorless, cannot be discriminated from the areas of air only by the shading differences of the image. The measuring system according to this invention provides the boundary calculating device for determining boundaries of the liquid whose image is picked up by the image pickup device. With such boundary calculating device provided, the boundaries of the separated liquid can be determined, and areas of the separated liquid can be determined accurately.

In the above measuring system according to this invention, the separating device is a flat plate grooved in a predetermined size. That is, since it is grooved in a predetermined size, if the boundary calculating device determines boundaries of the liquid fed into the flat plate, the area of the grooves or the volume of the grooves divided and grooved in the predetermined size can be specified.

When the above boundary calculating device determines the boundaries based on shading differences in the image of the separated liquid in the separating device (i.e. the flat plate) picked up by the image pickup device, the boundaries are determined with the following device.

That is, an edge enhancing device is provided for enhancing, as edges, the shading differences in the image of the separated liquid in the separating device picked up by the image pickup device, wherein the boundary calculating device determines the boundaries based on the image with the edges enhanced by the edge enhancing device. Thus, even though the separating device is limited to the flat plate, since the image with the edges enhanced by the edge enhancing device is used, the boundaries can be determined easily and accurately. Further, the following devices are provided for determining the boundaries accurately.

That is, the measuring system further comprises a flow path position extracting device. This flow path position extracting device, based on design information on the grooves having the predetermined size in the flat plate, and the flat plate, extracts flow path positions of the grooves by adjusting pixel positions of the grooves in the image with the edges enhanced by the edge enhancing device. Further, the boundary calculating device determines the boundaries based on the image in the pixel positions adjusted by the flow path position extracting device. In this case, with the flat plate grooved in the predetermined size, the design information of the grooves and the flat plate is known beforehand, and in other words, the flat plate has been grooved in the predetermined size based on this design information. By adjusting the pixel positions of the shading differences of the image using this design information, errors can be reduced to determine the boundaries with increased accuracy. Where only the above edge enhancing device is provided and the flow path position extracting device is not provided, not only the grooves (flow paths) but all that is included in the flat plate is edge-enhanced by the edge enhancing device. Therefore, edges of areas of the liquid to be divided are not fully enhanced. So, the flow path position extracting device extracts the flow path positions of the grooves by adjusting the pixel positions, to fully enhance the edges of the areas of the liquid to be divided, to facilitate determination of the boundaries.

One example of the above flat plate is a planar disk, and grooves are formed in the predetermined size radially of the disk. A rotating device may be disposed centrally of the disk for rotating the disk, the liquid to be measured being centrifuged using a centrifugal force of the disk generated by the rotating device. Further, one example of the liquid to be measured is blood, and plasma separation is carried out to centrifuge the blood and separate the blood into plasma and blood cell using the centrifugal force of the flat plate generated by the rotating device. As will be described hereinafter, the liquid to be measured is not limited to blood, but may be a liquid including a fluorescent agent, or a mixed liquid used in an analyzing apparatus, for example.

When the flow path position extracting device adjusts the pixel positions using the above design information, various examples can be adduced as follows.

For example, an edge enhancing device is additionally provided for enhancing, as edges, the shading differences of the image in the pixel positions adjusted by the flow path position extracting device, and the boundary calculating device determines as boundaries the edges enhanced by the edge enhancing device. In this case, since the edges enhanced by the edge enhancing device are determined as boundaries, the boundaries can be determined easily with increased accuracy.

In another example, a straight line drawing device is provided for drawing a plurality of straight lines parallel to the grooves on the image with the edges enhanced by the edge enhancing device which enhances, as the edges, the shading differences of the image in the pixel positions adjusted by the flow path position extracting device. The boundary calculating device may determine the boundaries based on a profile of the plurality of straight lines drawn by the straight line drawing device.

Where the edge enhancing device is provided for enhancing, as edges, the shading differences of the image in the pixel positions adjusted by the flow path position extracting device, this edge enhancing device acts as a second edge enhancing device. Further, the edge enhancing device which enhances, as the edges, the shading differences in the image of the separated liquid in the flat plate picked up by the image pickup device acts as a first edge enhancing device. This first edge enhancing device is an upstream edge enhancing device for enhancing, as edges, the shading differences of the image of the separated liquid in the flat plate picked up by the image pickup device. The second edge enhancing device is a downstream edge enhancing device for enhancing, as edges, the shading differences of the image in the pixel positions adjusted by the flow path position extracting device. Thus, the second edge enhancing device carries out edge enhancement after edge enhancement by the above first edge enhancing device. The boundary can be determined easily by carrying out the edge enhancement twice.

One example of the edge enhancing device carries out the edge enhancement by primary differential which determines differences between an attention pixel and its peripheral pixels. Another example carries out the edge enhancement by quadratic differential which determines further differences of the differences between the attention pixel and its peripheral pixels. As the edge enhancement by primary differential, a Sobel filter or a Prewitt filter may be used. The edge enhancing device is not limited to the edge enhancement by primary differential. As the above edge enhancement by quadratic differential, a Laplacian filter may be used. Thus, a device usually used for edge enhancement will serve the purpose, instead of being limited to the edge enhancement by primary differential or quadratic differential.

In these measuring systems according to this invention described above, it is preferable to provide a detecting device for simultaneously and two-dimensionally detecting the light or radiation included in the liquid to be measured to obtain two-dimensional image information of the light or radiation, and a superimposition processing device for carrying out a superimposition process to superimpose the image of the separated liquid in the separating device picked up by the image pickup device and a distribution image of the two-dimensional image information obtained by the detecting device, wherein, based on areas of the liquid divided by the boundary calculating device, and areas in the distribution image superimposed thereon, information on the light or radiation in these areas is obtained. With such superimposition process carried out, information on the light or radiation in these areas can be obtained accurately.

Where the above superimposition processing device is provided, and where one example of the liquid to be measured is blood including radiation, the following determination is made. The separating device carries out plasma separation which centrifuges and separates the blood into plasma and blood cell, and the boundary calculating device determines boundaries between plasma and blood cell. The detecting device simultaneously and two-dimensionally detects the radiation included in the blood to obtain two-dimensional image information of the radiation. The superimposition processing device carries out a superimposition process to superimpose the image resulting from the plasma separation and the distribution image of the two-dimensional image information obtained by the detecting device. Based on the plasma and blood cell divided by the boundary calculating device and the plasma and blood cell in the distribution image superimposed thereon, a radioactive concentration is determined for each of the plasma and blood cell.

Where the above superimposition processing device is provided, and where one example of the liquid to be measured is a liquid including a fluorescent substance, the following determination is made. The detecting device simultaneously and two-dimensionally detects light included in the liquid to obtain two-dimensional image information of the light. Based on areas of the liquid divided by the boundary calculating device and areas in the distribution image superimposed thereon, densities of the fluorescent substance in these areas are determined.

Effects of the Invention

The measuring system according to this invention includes a boundary calculating device for calculating boundaries of a separated liquid whose image has been picked up by an image pickup device. With such boundary calculating device provided, the boundaries of the separated liquid can be determined, and areas of the separated liquid can be determined accurately.

Further, the separating device is a flat plate grooved in a predetermined size, an edge enhancing device is provided for enhancing, as edges, the shading differences in the image of the separated liquid in the flat plate picked up by the image pickup device, a flow path position extracting device is provided for extracting, based on design information on grooves having the predetermined size in the flat plate, and the flat plate, flow path positions of the grooves by adjusting pixel positions of the grooves in the image with the edges enhanced by the edge enhancing device, and the boundary calculating device determines the boundaries based on the image in the pixel positions adjusted by the flow path position extracting device. In this case, with the flat plate grooved in the predetermined size, the design information of the grooves and the flat plate is known beforehand, and in other words, the flat plate has been grooved in the predetermined size based on this design information. By adjusting the pixel positions of the shading differences of the image using this design information, errors can be reduced to determine the boundaries with increased accuracy.

DESCRIPTION OF REFERENCES

Figure 1:
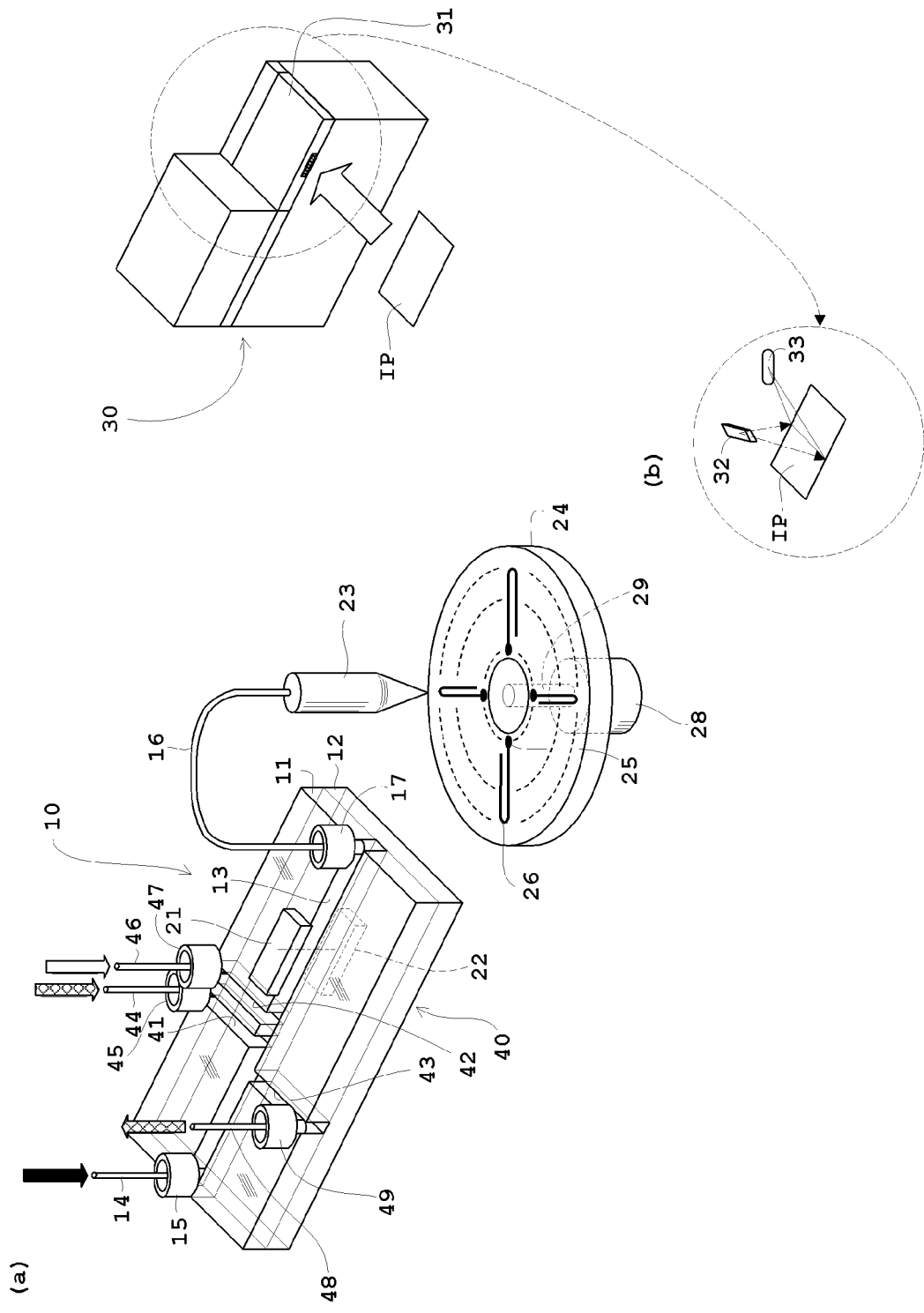
FIG. 1 is an outline perspective view of a blood collecting apparatus and a measuring apparatus according to an embodiment.

24 . . . disk
26 . . . grooves
28 . . . motor
31 . . . reading unit
34 . . . image pickup unit
35a, 35b . . . Sobel filter
36 . . . flow path position extracting unit
37 . . . straight line drawing unit
38 . . . boundary calculating unit
39 . . . superimposition processing unit
$p_{22}$ . . . central pixel
IP . . . imaging plate Embodiment An embodiment of this invention will be described hereinafter with reference to the drawings.

Figure 2:
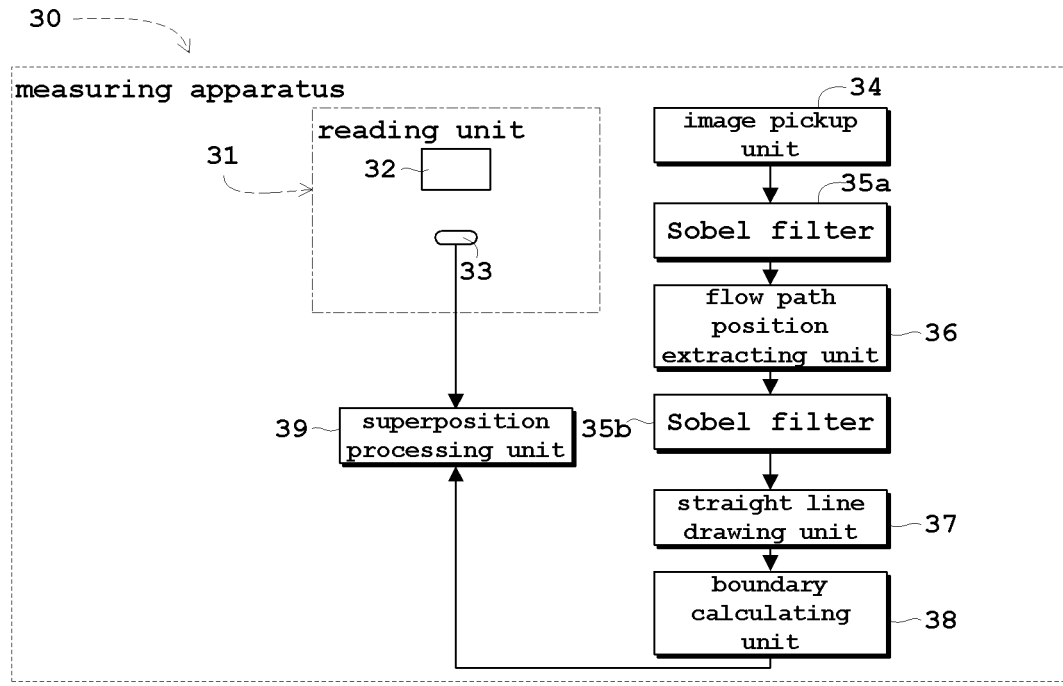
FIG. 2 is a block diagram of the measuring apparatus according to the embodiment.
Figure 3:
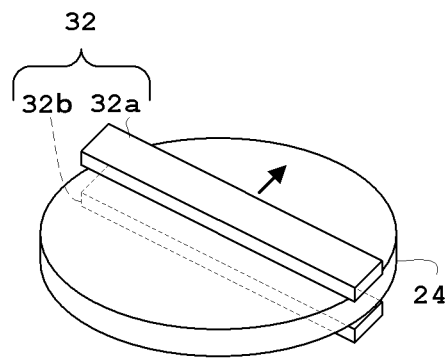
FIG. 3 is a schematic perspective view of a scanner in an image pickup unit of the measuring apparatus.

FIG. 1 is an outline perspective view of a blood collecting apparatus and a measuring apparatus according to the embodiment. FIG. 2 is a block diagram of the measuring apparatus according to the embodiment. FIG. 3 is a schematic perspective view of a scanner in an image pickup unit of the measuring apparatus. This embodiment will be described, taking blood as an example of liquid to be measured, and taking a system having a blood collecting apparatus and a measuring apparatus as an example of measuring system.

As shown in FIG. 1, a blood collecting apparatus 10 according to this embodiment collects blood to be measured, as separated in a time series. Around the blood collecting apparatus 10, a measuring apparatus 30 is provided for measuring radiation (e.g. β-rays, γ-rays or the like) included in the blood collected by the blood collecting apparatus 10. In this embodiment, blood is collected after introducing a radioactive drug into the body of a mouse, and radiation included in the blood is measured. Further, a plasma separation by centrifugal separation is carried out, and each of the radiations included in the plasma and blood cell resulting from the plasma separation is measured.

The blood collecting apparatus 10 has a liquid dividing device 40 formed of two PDMS substrates 11 and 12 of PDMS (Polydimethylsiloxane) resin, one superposed on the other. The PDMS substrates 11 and 12 are grooved in a predetermined size, and grooves resulting from the grooving form a main flow path 13 and side paths 41, 42 and 43. Here, the material for the blood collecting apparatus 10 is not limited to PDMS, but may be any resin optically transparent material such as acrylic, polycarbonate, COP (cycloolefin polymer) or the like.

A catheter 14 is disposed at a blood inlet of the main flow path 13, and the main flow path 13 and catheter 14 are connected through a connector 15. Blood is continuously fed from the catheter 14 into the main flow path 13, and its inflow volume is controlled by a valve (not shown). Blood piping 16 is disposed at a blood outlet of the main flow path 13, and the main flow path 13 and blood piping 16 are connected through a connector 17.

A light source 21 and a photodiode 22 are opposed to each other across the main flow path 13. Light is emitted from the light source 21 to the blood, or a heparin solution to be described hereinafter, flowing through the main flow path 13, and the photodiode 22 detects light-shielding by the blood, thereby to measure length information on the blood or heparin solution described hereinafter while optically monitoring the blood or heparin solution. Although the light source 21 and photodiode 22 have been described here as an example of the optical measuring device, the light source 21 and photodiode 22 are not limitative as long as the device measures the intervals of the liquid while optically monitoring the liquid to be measured. For example, volume information of the liquid to be measured may be acquired with a CCD camera. The light source 21 and photodiode 22 are opposed to each other across the main flow path 13 as shown in FIG. 1, to constitute what is called a "transmission type sensor" for making detection based on light-shielding by the blood. Instead, what is called a "reflection type sensor" may be used to detect light reflected by the blood, with a light detecting device represented by a photodiode arranged at the same side as the light source.

On the other hand, a dispenser 23 is connected downstream of the above blood piping 16. Although the dispenser 23 is used to drip the liquid here, a capillary tube such as a hypodermic needle or glass tube may be used. A disk (also called "CD well") 24 is disposed for receiving and storing the blood dripping from this dispenser 23. The disk 24 has a plurality of openings 25 arranged centrally and radially thereof for receiving the dripping blood. The disk 24 is grooved, as is the above PDMS substrates 11 and 12, and a plurality of U-shaped grooves 26 are formed radially by the grooving. Each U-shaped groove 26 is connected in a one-to-one relationship to one outer end of the above opening 25, and each U-shaped groove 26 is formed to extend radially of the disk 24. With the dispenser 23 interposed in this way, the disk 24 is formed capable of circulating blood with respect to the main flow path 13. The disk 24 corresponds to the separating device in this invention, and also to the flat plate in this invention. A specific construction of the disk 24 will be described hereinafter with reference to FIG. 4 et seq.

On the other hand, the measuring apparatus 30 has a reading unit 31. This reading unit 31 has a cover for inserting an exposed imaging plate IP, and detects β$^+$ rays included in the blood by reading excited light from the imaging plate IP. Specifically, as shown in FIG. 1 (b), the reading unit 31 has a laser light source 32 and a photomultiplier tube 33. β$^+$ rays are simultaneously detected in two dimensions by emitting laser from the laser light source 32 to the imaging plate IP, with the photomultiplier tube 33 converting to and multiplying electrons, the light excited by the laser emission to the imaging plate IP. The imaging plate IP and reading unit 31 correspond to the detecting device in this invention.

A block diagram of the measuring apparatus 30 will be described next. As shown in FIG. 2, the measuring apparatus 30 includes, besides the above reading unit 31, an image pickup unit 34, Sobel filters 35a and 35b, a flow path position extracting unit 36, a straight line drawing unit 37, a boundary calculating unit 38, and a superimposition processing unit 39. The image pickup unit 34 corresponds to the image pickup device in this invention. The Sobel filters 35a and 35b correspond to the edge enhancing devices in this invention. The flow path position extracting unit 36 corresponds to the flow path position extracting device in this invention. The straight line drawing unit 37 corresponds to the straight line drawing device in this invention. The boundary calculating unit 38 corresponds to the boundary calculating device in this invention. The superimposition processing unit 39 corresponds to the superimposition processing device in this invention. The upstream Sobel filter 35a of the Sobel filters 35a and 35b corresponds also to the first edge enhancing device in this invention. The downstream Sobel filter 35b corresponds also to the second edge enhancing device in this invention.

As shown in FIG. 3, the image pickup unit 34 picks up an image of the disk 24. In this embodiment, a flathead scanner is employed as the image pickup unit 34. The flathead scanner includes a linear light source 32a having a length at least corresponding to the diameter of the disk 24, and a linear photodiode array (i.e. a line sensor) 32b opposed to the light source 32a across the disk 24. The flathead scanner scans over the disk 24 to pick up an image of the disk 24, thereby acquiring the image of the disk 24.

The upstream Sobel filter 35a, in order to enhance, as edges, the shading differences of the image picked up by the image pickup unit 34 of the U-shaped grooves 26 (see FIG. 1) grooved in the disk 24, carries out a Sobel filter process as edge enhancement by primary differential which determines differences between an attention pixel and its peripheral pixels. The Sobel filter process by the Sobel filter 35a will be described hereinafter with reference to FIG. 7 et seq.

The flow path position extracting unit 36, based on design information on the grooves 26 having a predetermined size on the disk 24 and the disk 24 in the image picked up by the image pickup unit 34, extracts flow path positions of the grooves 26 by adjusting pixel positions in the image with the edges enhanced by the Sobel filter 35a. The flow path position extraction by the flow path position extracting unit 36 will also be described hereinafter with reference to FIG. 7 et seq.

The downstream Sobel filter 35b carries out a Sobel filter process as edge enhancement by primary differential in order to enhance, as edges, the shading differences of the image in the pixel positions adjusted by the flow path position extracting unit 36. The Sobel filter process by the Sobel filter 35b will also be described hereinafter with reference to FIG. 7 et seq.

The straight line drawing unit 37 draws a plurality of straight lines parallel to the grooves 26 on the image with the edges enhanced by the Sobel filter 35b. The straight line drawing by the straight line drawing unit 37 will also be described hereinafter with reference to FIG. 7 et seq.

The boundary calculating unit 38 determines boundaries of the separated liquid based on a profile of the plurality of straight lines drawn by the straight line drawing unit 37. In this embodiment, boundaries between the plasma and the blood cell resulting from the plasma separation are determined. The boundary calculation by the boundary calculating unit 38 will also be described hereinafter with reference to FIG. 7 et seq.

The superimposition processing unit 39 obtains count information on $\beta^+$ rays per unit volume, based on the image picked up by the image pickup unit 34 and processed through the Sobel filter 35a, flow path position extracting unit 36, Sobel filter 35b, straight line drawing unit 37, and boundary calculating unit 38, and count information on $\beta^+$ rays obtained by the imaging plate IP and reading unit 31. Specifically, the superimposition processing unit 39 carries out a superimposing process to superimpose the image processed through the image pickup unit 34, Sobel filter 35a, flow path position extracting unit 36, Sobel filter 35b, straight line drawing unit 37, and boundary calculating unit 38, and a distribution image of the count information on $\beta^+$ rays obtained by the imaging plate IP and reading unit 31. At the time of this superimposition process, a radioactive concentration in each of the plasma and blood cell is determined based on the plasma and blood cell divided by the boundary calculating unit 38 and the plasma and blood cell in the distribution image superimposed thereon.

Returning to the description of FIG. 1, the liquid dividing device 40 has the main flow path 13 for feeding blood, a side path 41 for feeding the heparin solution which is a type of anticoagulant for preventing an occurrence of blood coagulation, a side path 42 for feeding air or gas, and a side path 43 for discharging the blood or heparin solution.

Cleaning solution piping 44 is disposed at a solution inlet of the side path 41, and the side path 41 and cleaning solution piping 44 are connected through a connector 45. The flow paths are cleaned as necessary by pouring the heparin solution from the cleaning solution piping 44 through the side path 41 into the main flow path 13. Inflow volume of the heparin solution is controlled by a valve. The anticoagulant is not limited to the heparin solution.

Bubble piping 46 is disposed at a gas inlet of the side path 42, and the side path 42 and bubble piping 46 are connected through a connector 47. Air or gas controlled by a pressure generator (not shown) is fed through the side path 42 into the main flow path 13, with its feed time adjusted by a valve. With these bubbles, blood is extracted based on length information on the blood, and waste liquids (blood, heparin solution or mixture of these) remaining in the flow paths of the liquid dividing device 40 are discharged. There is no limitation regarding the gas to be fed, but may be any gas that does not react with blood or heparin solution, which may be a rare gas such as helium, neon or argon, or nitrogen gas, for example.

The bubble piping 46 feeds the gas (e.g. air or gas) into the main flow path 13 through the side path 42, introducing the gas as bubbles at specified predetermined intervals, thereby feeding the blood to be measured, as separated in a time series, to the disk 24. That is, the bubbles perform a function as separators. Although a gas is used as the separators, instead of being limited to the gas, a liquid other than the liquid to be measured may be used as the separators as long as this liquid has little or no chance of mixing with the liquid to be measured (blood in this embodiment). Where the liquid to be measured is blood as in this embodiment, a liquid represented by mineral oil, fluorine-based oil or the like, which does not mix with blood, may be used as the separators. However, using a liquid as the separators, although this is possible, is not desirable in terms of feeding to and collecting from the disk 24 because of contact with blood.

Waste liquid piping 48 is disposed at a waste liquid outlet of the side path 43, and the side path 43 and waste liquid piping 48 are connected through a connector 49. An amount of discharge is adjusted with a valve, to discharge as waste liquid part of blood other than the blood to be collected, the heparin solution after flow path cleaning, and a mixture of these.

A valve is disposed downstream of the connector 15 of the main flow path 13. A valve is disposed upstream of the connector 17, light source 21 and photodiode 22 of the main flow path 13. A valve is disposed downstream of the connector 45 of the side path 41. A valve is disposed downstream of the connector 47 of the side path 42. A valve is disposed upstream of the connector 49 of the side path 43.

Figure 4:
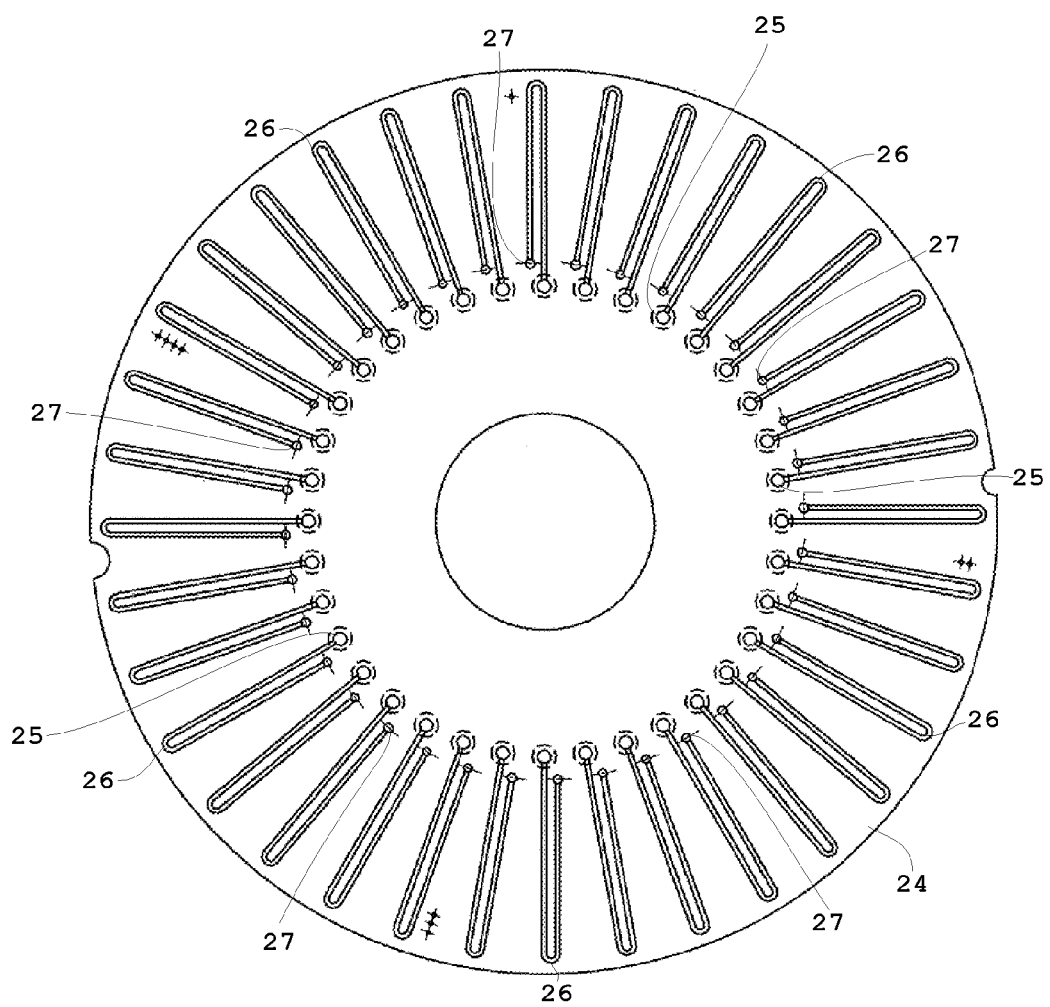
FIG. 4 is a schematic plan view of a disk according to the embodiment.
Figure 5:
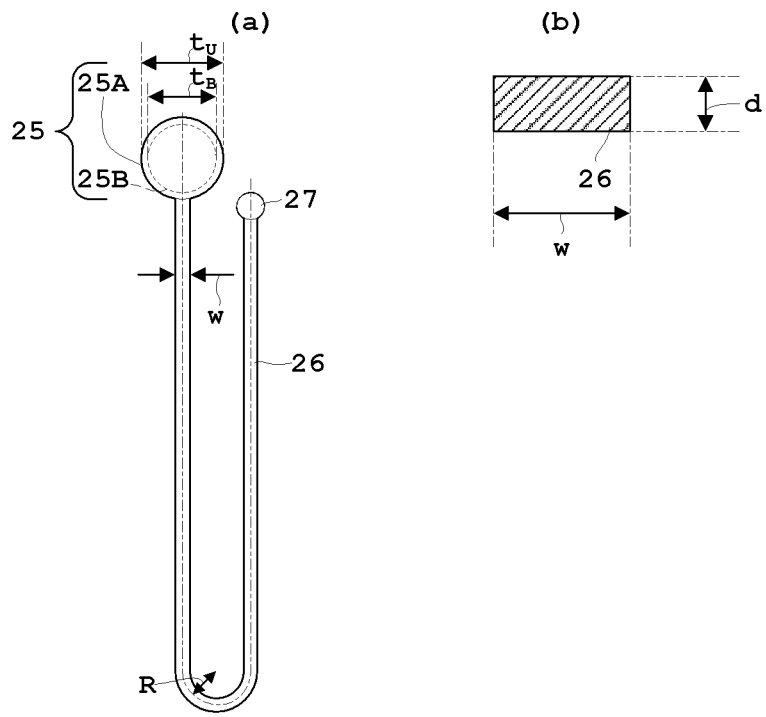
FIG. 5 (a) is a schematic plan view of a U-shaped groove according to the embodiment, and (b) is a schematic enlarged sectional view of the U-shaped groove according to the embodiment.
Figure 6:
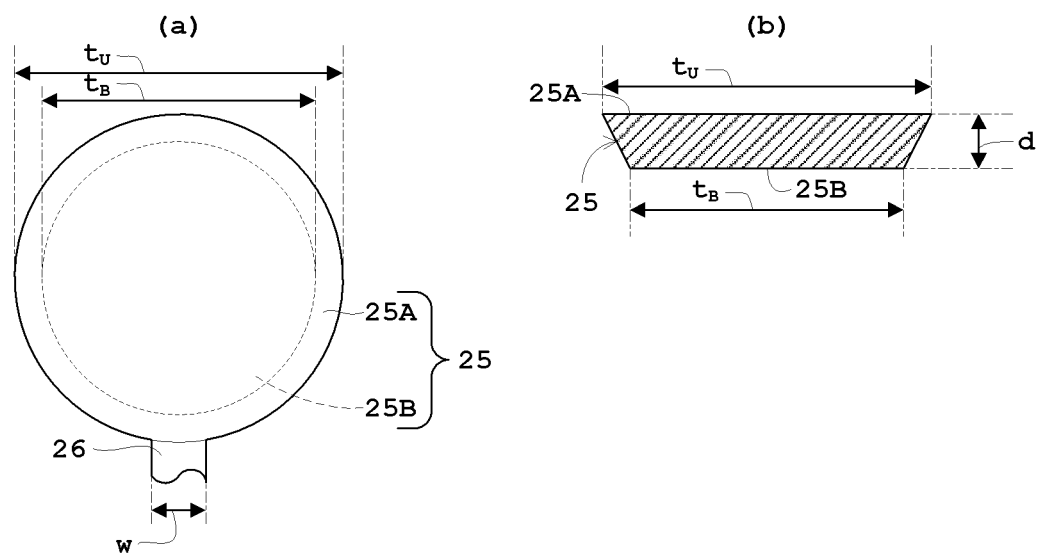
FIG. 6 (a) is a schematic plan view of an opening according to the embodiment, and (b) is a schematic sectional view of the opening according to the embodiment.

Next, a specific construction of the disk 24 will be described with reference to FIGS. 4-6 as well as FIG. 1. FIG. 4 is an outline plan view of the disk according to the embodiment. FIG. 5 (a) is an outline plan view of a U-shaped groove according to the embodiment. FIG. 5 (b) is a schematic enlarged sectional view of the U-shaped groove according to the embodiment. FIG. 6 (a) is a schematic plan view of an opening according to the embodiment. FIG. 6 (b) is a schematic sectional view of the opening according to the embodiment.

As shown in FIGS. 4-6, the grooves 26 of the disk 24 are formed to connect the openings 25 described hereinbefore and air holes 27. The grooves 26 are U-shaped so that, when the openings 25 acting as blood feed ports are regarded as being located upstream, and the air holes 27 as being located downstream, each groove 26 extends from upstream to downstream, i.e. from a radially inward position to a radially outward position of the disk 24, and then turns back to extend radially inward from the radially outward position of the disk 24. A plurality of such grooves 26 are provided.

As shown in FIG. 1, a motor 28 is provided centrally of the disk 24 for rotating the disk 24. The motor 28 has a rotary shaft 29 connected to the disk 24, whereby the centrifugal force of the disk 24 generated by the motor 28 is used to carry out plasma separation to centrifuge the blood into plasma and blood cell. The motor 28 corresponds to the rotating device in this invention.

In this embodiment, the plurality of grooves 26 are arranged radially of the disk 24 as shown in FIG. 4. As described hereinbefore, the plurality of grooves 26 are formed by grooving the disk 24 in a predetermined size.

More particularly, the width of each groove 26 is set to was shown in the plan view of FIG. 5 (a) and the plan view of FIG. 6 (a), and the depth of each groove 26 is set to h as shown in the sectional view of FIG. 5 (b) and the sectional view of FIG. 6 (b). As shown in FIG. 6, with the diameter of an upper plane 25A of each opening 25 set to $t_U$, and the diameter of a lower plane 25B set to $t_B$, each opening 25 is formed in a tapered shape having the upper plane 25A larger than the lower plane 25B. As shown in the plan view of FIG.

5 (a), the curvature radius of the curved portion where each groove 26 turns back is set to R. The curvature radius here is a distance to the center of groove 26.

In this embodiment, the disk 24 is formed by pressure bonding together a 1 mm thick acrylic plate having 36 grooves 26 whose width w is 0.5 mm and depth d is 0.2 mm, and length is 40 mm, and a 0.2 mm thick acrylic plate, one superposed on the other. Thus, 36 U-shaped grooves 26 (U-shaped minute volume flow paths) are formed. The disk 24 is 104 mm in diameter, and the curvature radius R of the curved portion where each groove 26 turns back is 0.75 mm. A hydrophilization process is carried out for inner walls of the grooves 26 with an excimer lamp. Each opening 25 has a tapered shape with the upper plane 25A larger than the lower plane 25B, the diameter $t_U$ of the upper plane 25A being 2.6 mm, and the diameter $t_B$ of the lower plane 25B being 1.5 mm. The above hydrophilization process is not limited to use of the excimer lamp. Any usual hydrophilization process may be employed, such as a process with a drug, plasma treatment or ultraviolet irradiation, for example.

Figure 7:
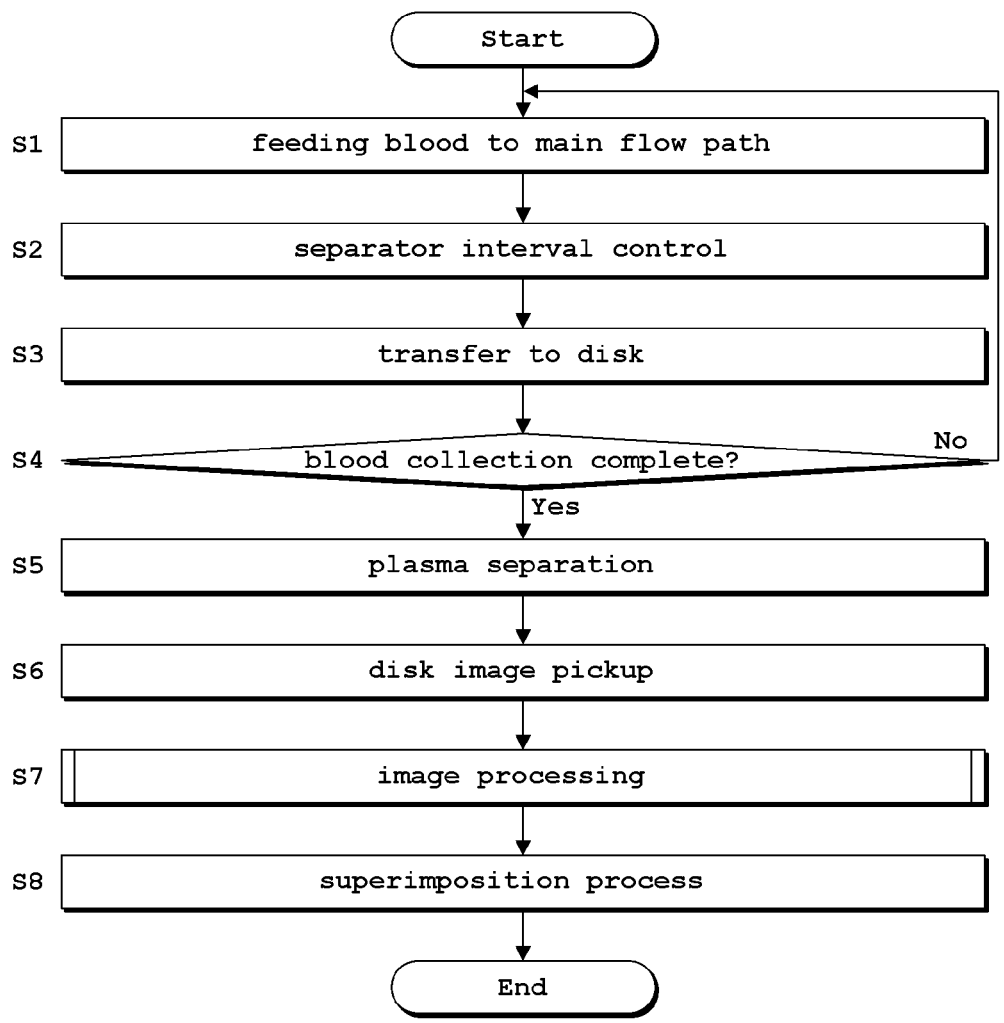
FIG. 7 is a flow chart showing a sequence of a series of blood collecting steps according to the embodiment.
Figure 8:
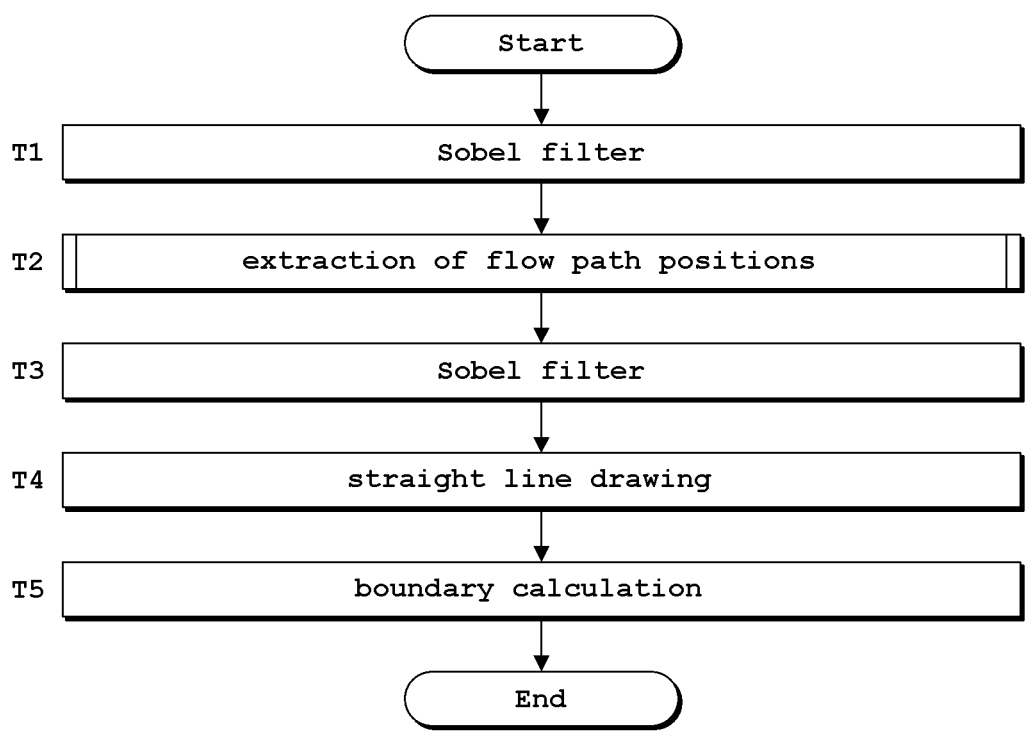
FIG. 8 is a flow chart showing a sequence of a series of image processing steps according to the embodiment.
Figure 9:
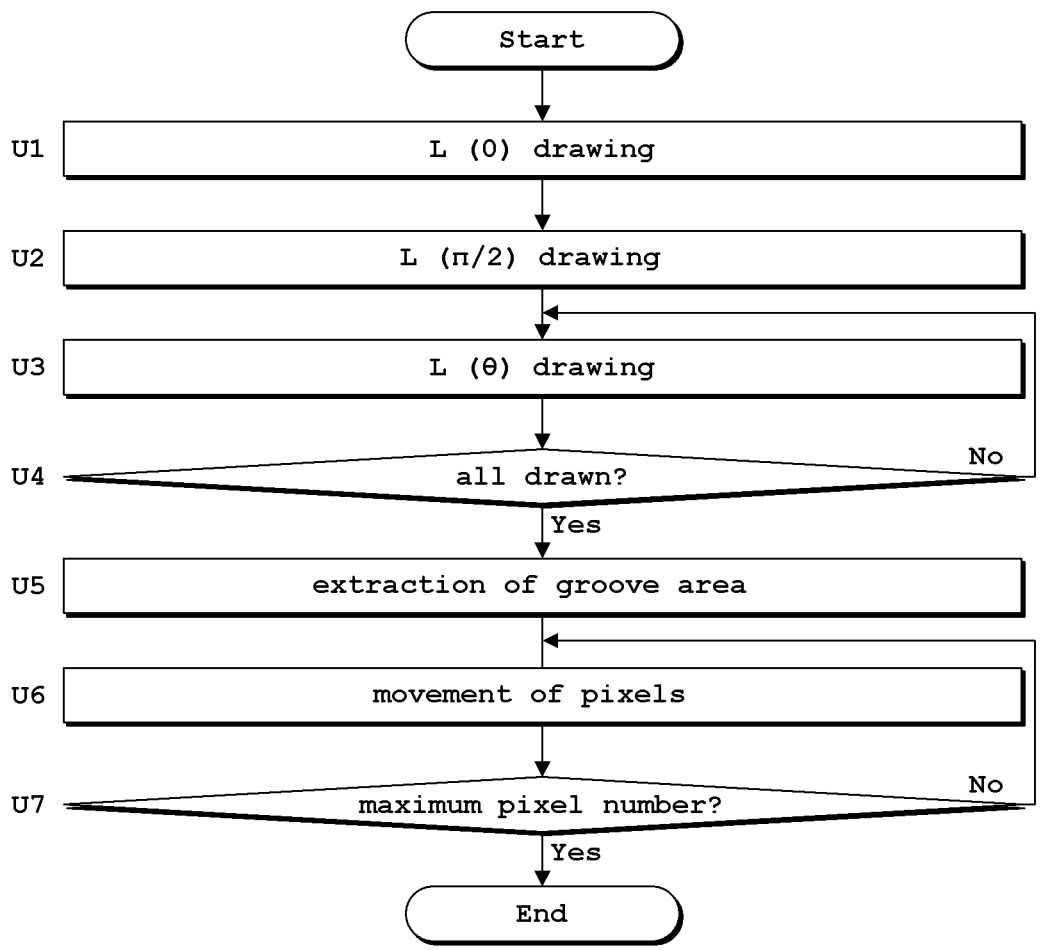
FIG. 9 is a flow chart showing a sequence of a series of flow path position extracting steps according to the embodiment.
Figure 10:
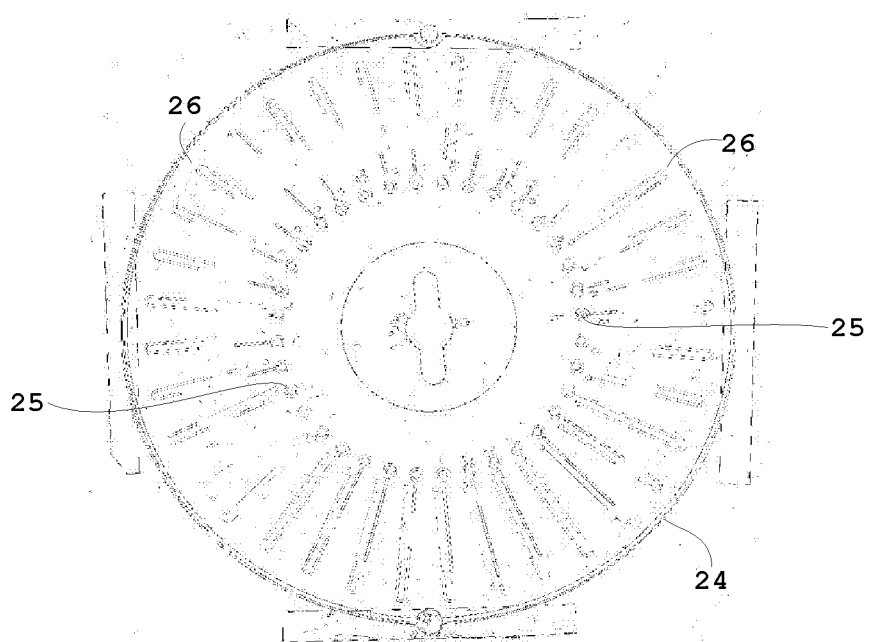
FIG. 10 is a schematic view showing a black-and-white reversal of the disk (image) with enhanced edges after a Sobel filter process relating to step T1 in FIG. 8.
Figure 11:
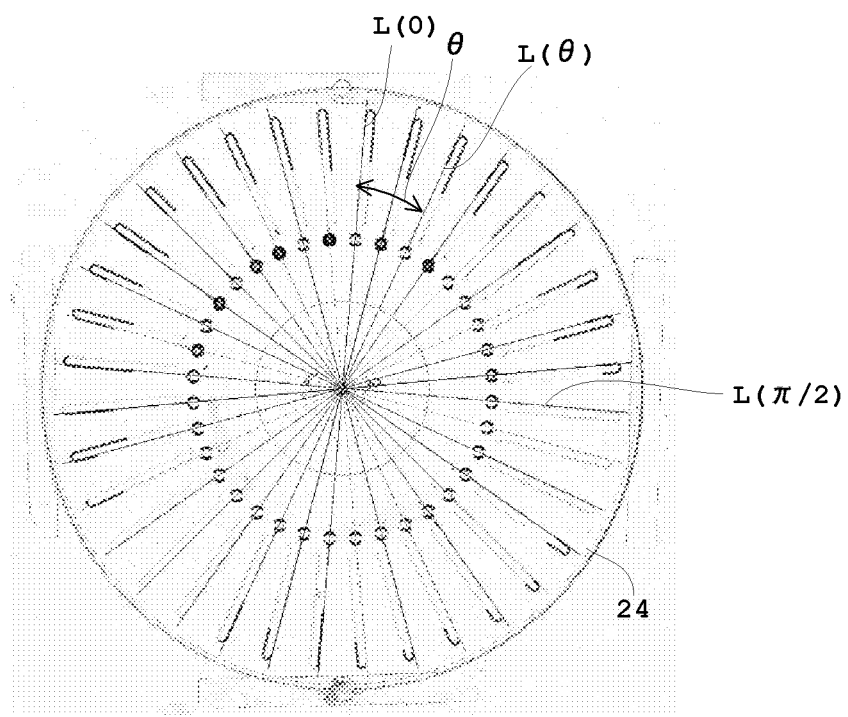
FIG. 11 is a schematic plan view of a straight line drawing and the disk relating to steps U1-U4 in FIG. 9.
Figure 12:
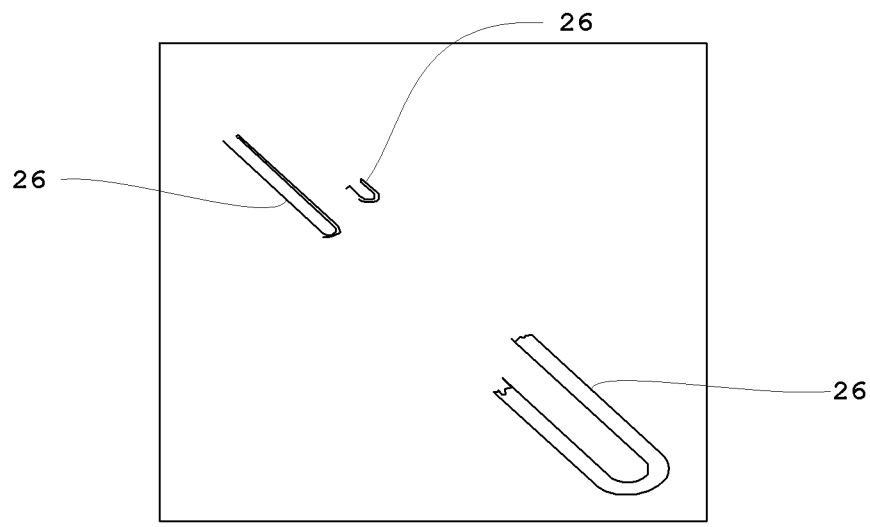
FIG. 12 is a schematic view showing a black-and-white reversal of the disk (image) with enhanced edges after a Sobel filter process relating to step T3 in FIG. 8.
Figure 13:
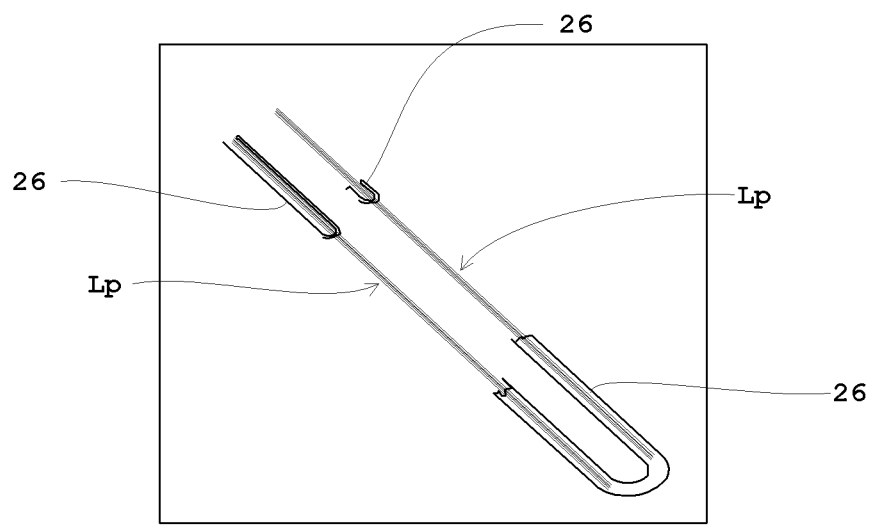
FIG. 13 is a schematic view showing a black-and-white reversal of a straight line drawing and the disk relating to step T4 in FIG. 8.
Figure 14:
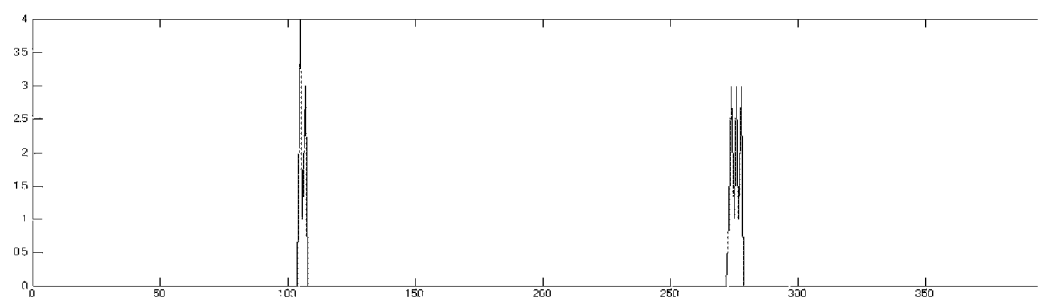
FIG. 14 is a profile based on a straight line group having a plurality of straight lines drawn in step T4 in FIG. 8.
Figure 15:
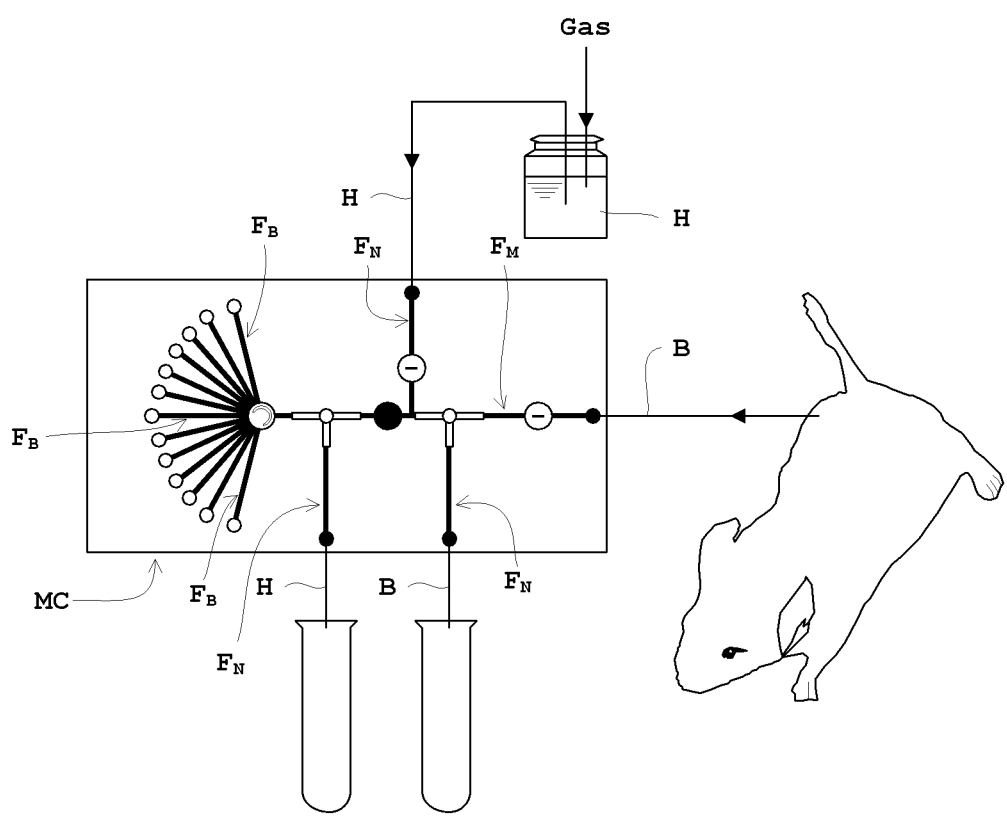
FIG. 15 is a plan view showing an entire microchip construction at the time of a conventional microfluidic device mode.

Next, a series of blood collecting steps will be described with reference to FIGS. 7-14. FIG. 7 is a flow chart showing a sequence of the series of blood collecting steps according to the embodiment. FIG. 8 is a flow chart showing a sequence of a series of image processing steps according to the embodiment. FIG. 9 is a flow chart showing a sequence of a series of flow path position extracting steps according to the embodiment. FIG. 10 is a schematic view showing a black-and-white reversal of the disk (image) with enhanced edges after a Sobel filter process relating to step T1 in FIG. 8. FIG. 11 is a schematic plan view of a straight line drawing and the disk relating to steps U1-U4 in FIG. 9. FIG. 12 is a schematic view showing a black-and-white reversal of the disk (image) with enhanced edges after a Sobel filter process relating to step T3 in FIG. 8. FIG. 13 is a schematic view showing a black-and-white reversal of a straight line drawing and the disk relating to step T4 in FIG. 8. FIG. 14 is a profile based on a straight line group having a plurality of straight lines drawn in step T4 in FIG. 8.

(Step S1) Feeding Blood to Main Flow Path

Blood is continuously fed into the main flow path 13 by inserting the catheter 14 (see FIG. 1) into a mouse artery, and directing arterial blood delivering itself under mouse blood pressure to the main flow path 13 (see FIG. 1) through the catheter 14.

(Step S2) Separator Interval Control

When blood is not flowing through the main flow path 13 (see FIG. 1), the light emitted from the light source 21 (see FIG. 1) falls on the photodiode 22 (see FIG. 1) opposed to the light source 21 across the main flow path 13. Therefore, a detector signal having undergone photoelectric conversion by the photodiode 22 is outputted at high level from the photodiode 22. Conversely, when blood is flowing through the main flow path 13, the light emitted from the light source 21 is shielded by the blood. Since the light does not fall on the photodiode 22, the detector signal is outputted at low level from the photodiode 22. With the photodiode 22 detecting the light-shielding by the blood, length information on the blood is measured while optically monitoring the blood. The valve is controlled based on the measurement result by the photodiode 22. By controlling the valve, intervals at which air or gas fed from the side path 42 into the main flow path 13, i.e. the intervals of the separators, are controlled. Since the main flow path 13 is formed by grooving in a predetermined size, a volume of the blood to be taken out is derived from the blood length information obtained by optical monitoring.

(Step S3) Transfer to Disk

Very small amounts of blood taken out in step S2 are fed into the dispenser 23 (see FIG. 1) through the blood piping 16 (see FIG. 1). The dispenser 23 drips each very small amount of the taken-out blood to an opening 25 (see FIG. 1) of the disk (CD well) 24 (see FIG. 1). By this dripping, the very small amounts of the taken-out blood are transferred to the disk 24.

(Step S4) Completion of Blood Collection

Determination is made as to whether the blood collection is completed at a predetermined time. If the blood collection is not completed, the operation returns to step S1. If the blood collection is completed, the operation proceeds to the following step S5.

(Step S5) Plasma Separation

After the blood collection is all completed at the predetermined time, the blood is transferred to the disk 24 (see FIG. 1). Then, the disk 24 is rotated to carry out plasma separation for separating the blood into plasma and blood cell.

The catheter 14 (see FIG. 1) is cleaned, as necessary, or the heparin solution and air or gas are fed to discharge waste liquids (blood, heparin solution, or mixture of these) remaining in the flow paths of the liquid dividing device 40.

(Step S6) Disk Image Pickup

Each disk 24 (see FIG. 1) with the plasma and blood cell having undergone the plasma separation is, as a sample, put into an open cassette not shown, an imaging plate IP (see FIG. 1) is placed on the sample, and the cassette is closed for exposure. Through this exposure, electrons are captured by lattice defects of a phosphor (not shown) of the imaging plate IP with the ionization power of $\beta^+$ rays included in the blood. After a fixed time of exposure, the imaging plate IP is taken out of the cassette, and is inserted into the cover of the reading unit 31 (see FIG. 1) of the measuring apparatus 30 (see FIG. 1), and the imaging plate IP is exposed to light emitted thereto.

The laser light source 32 (see FIG. 1) of the reading unit 31 (see FIG. 1) emits laser to the imaging plate IP (see FIG. 1). The captured electrons are excited by this irradiation to conductors to recombine with holes, which are excited as light from the phosphor. The photomultiplier tube 33 (see FIG. 1) converts the light excited by the laser irradiation of the imaging plate IP into electrons and multiplies the electrons, thereby simultaneously detecting the electrons in two dimensions and counting them as electric pulses. After laser is emitted from the laser light source 32 to the imaging plate IP, the captured electrons are erased by light emitted from an erasing light source (not shown) to the imaging plate IP for reuse. Based on count information on $\beta^+$ rays obtained from the imaging plate IP and reading unit 31, a dose of radiation in the blood which is count information on $\beta^+$ rays is obtained.

The image pickup unit 34 (see FIGS. 2 and 3) picks up an image of the plasma and blood cell resulting from the plasma separation for each disk 24 (see FIG. 1). By emitting light from the light source 32a (see FIG. 3) of the flathead scanner of the image pickup unit 34, differences in absorbance cause the plasma and blood cell to appear as shading differences on the image picked up, which can be distinguished easily on the image. Based on the shading differences (that is, differences in absorbance) of the image in the grooves 26 (see FIG. 1) of the disk 24 picked up by the image pickup unit 34, image processing is carried out by the Sobel filter 35a, flow path position extracting unit 36, Sobel filter 35b, straight line drawing unit 37, and boundary calculating unit 38.

(Step S7) Image Processing

The image processing in step S7 will be described with reference to the flow chart of FIG. 8.

(Step T1) Sobel Filter

The upstream Sobel filter 35a carries out a Sobel filter process in order to enhance as edges the shading differences of the image of the separated blood in the disk 24 picked up by the image pickup unit 34. It extracts 9 pixels consisting of 3×3 longitudinal and transverse pixels from the picked-up image, and carries out a matrix operation on these pixels as in the following equation (1).

[Math 1]

$$P = \begin{pmatrix} p_{11} & p_{12} & p_{13} \\ p_{21} & p_{22} & p_{23} \\ p_{31} & p_{32} & p_{33} \end{pmatrix},$$

$$Gh = \begin{pmatrix} -1 & 0 & 1 \\ -2 & 0 & 2 \\ -1 & 0 & 1 \end{pmatrix},$$

$$Gv = \begin{pmatrix} -1 & -2 & -1 \\ 0 & 0 & 0 \\ 1 & 2 & 1 \end{pmatrix}$$

(1)

In the above equation (1), P is a 3×3 longitudinal and transverse arrangement of pixel values $p_{11}$, $p_{12}$, $p_{13}$, $p_{21}$, $p_{22}$, $p_{23}$, $p_{31}$, $p_{32}$ and $p_{33}$ of the 9 pixels, and pixel $p_{22}$ in the center is regarded as the attention pixel serving as the object of the Sobel filter process. That is, the Sobel filter 35a, also including the downstream Sobel filter 35b, carries out edge enhancement by primary differential which determines differences between the attention pixel $p_{22}$ and its peripheral pixels $p_{11}$, $p_{12}$, $p_{13}$, $p_{21}$, $p_{23}$, $p_{31}$, $p_{32}$ and $p_{33}$.

[Math 2]

$$ph_{22} = \sum_{i=1}^{3} \sum_{j=1}^{3} p_{ij} Gh_{ij},$$

$$pv_{22} = \sum_{i=1}^{3} \sum_{j=1}^{3} p_{ij} Gv_{ij}$$

(2)

In the above equation (1), Sobel filter is divided into horizontal matrix Gh and vertical matrix Gv, operations are carried out by Gh and Gv on the attention pixel and its peripheral pixels. Attention pixel value $ph_{22}$ after the horizontal matrix Gh operation and each pixel value $pv_{22}$ after the vertical matrix Gv operation are expressed as in the above equations (2).

An image having edges enhanced horizontally is obtained by carrying out the horizontal matrix Gh operation, and an image having edges enhanced vertically is obtained by carrying out the vertical matrix Gv operation. Therefore, attention pixel $p'_{22}$ having edges enhanced horizontally and vertically is obtained by calculating the square root of the sum of squares of attention pixel $ph_{22}$ after the horizontal matrix Gh operation and attention pixel $pv_{22}$ after the vertical matrix Gv operation, as in the following equation (3).

[Math 3]

$$p'_{22} = \sqrt{ph_{22}^2 + pv_{22}^2}$$

(3)

The Sobel filter process is carried out by the Sobel filter 35a to perform calculations using the same method for other pixels, thereby to enhance the shading differences of the image as edges. An image of the disk 24 with enhanced edges after the Sobel filter process by the Sobel filter 35a is as shown in FIG. 10. Although it is in black-and-white reversal in practice, for expediency of illustration, FIG. 10 shows it schematically in black-and-white reversal. As shown in FIG. 10, the edges of the disk 24 are enhanced. At the stage of this step T1, all that is included in the disk 24 is edge-enhanced, and therefore areas of plasma and blood cell are not fully enhanced. So, boundaries between plasma and blood cell will be obtained through further steps T2 et seq.

(Step T2) Extraction of Flow Path Positions

Based on the design information of the grooves 26 having the predetermined sizes on the disk 24 and the disk 24 imaged by the image pickup unit 34, the flow path position extracting unit 36 extracts flow path positions of the grooves 26 by adjusting pixel positions in the image having the edges enhanced by the Sobel filter 35a in step T1. The extraction of flow path positions by the flow path position extracting unit 36 in step T2 will be described with reference to the flow chart of FIG. 9.

(Step U1) L (0) Drawing

On the image with the edges enhanced by the Sobel filter 35a in step T1, a straight line is drawn for two opposed flow paths (grooves 26). In time of drawing, while shifting the position and angle of the straight line, a position where the straight line most overlaps edges of the two opposed flow paths (grooves 26) is searched. Since the edges of the grooves 26 are enhanced in the areas of blood cell, it is easy to search the position where the straight line overlaps most and to draw the straight line. The straight line drawn in this way is regarded as L (0) as shown in FIG. 11. Here, L ($\theta$) denotes a straight line drawn at angle $\theta$ [rad] to L (0). Therefore, L ($\pi/2$) which will be described hereinafter is a straight line drawn at angle $\pi/2$ [rad] (=90°) to L (0).

(Step U2) L ($\pi/2$) Drawing

Next, a second straight line is drawn which is turned $\pi/2$ [rad] (=90°) relative to L (0) drawn in step U1. With the same method as in step U1, a position where the straight line most overlaps edges of the two opposed flow paths (grooves 26) is searched. Since this straight line is a straight line drawn at angle $\pi/2$ [rad] (=90°) to L (0), it becomes L ($\pi/2$). The intersection of the above two straight lines L (0) and L ($\pi/2$) is the center of the disk (CD well) 24.

(Step U3) L ($\theta$) Drawing

Straight lines L ($\theta$) are drawn for the grooves 26 providing all the flow paths, while turning each straight line by $\theta$ [rad]. Since there are 36 grooves 26 in total in this embodiment, when one straight line is drawn for two opposed flow paths (grooves 26), a total of 18 straight lines will be drawn including L (0) and ($\pi/2$). Therefore, in this embodiment, straight lines L ($\theta$) are drawn, while turning each by angle $\pi/18$ [rad] (=10°).

(Step U4) All Drawn?

Whether all the straight lines L ($\theta$) have been drawn is checked. When all have been drawn, the operation proceeds to the next step U5. When the drawing is not completed, the operation returns to step U3 and repeats steps U3 and U4 until all (in this case, a total of 18) straight lines L ($\theta$) are drawn.

(Step U5) Extraction of Groove Area

Based on the design information on the grooves 26 and disk 24, a circle is drawn in an outer diameter position from the intersection (the center of the disk 24) of the straight lines L (0) and L ($\pi/2$) determined in step U2. An image of the disk 24 on which straight lines are drawn as shown in FIG. 11 is created by the processes in steps U1-U4 and step U5. And the area of the U-shaped grooves 26 (U-shaped minute volume flow paths) is extracted from the intersection (the center of the disk 24) of the straight lines L (0) and L ($\pi/2$) determined based on the design information on the grooves 26 in step U2, and the straight lines L ($\theta$) drawn in steps U1-U4.

(Step U6) Movement of Pixels

Since the groove area (flow path area) extracted in step U5 is with an error, the pixels in the area are moved horizontally up and down and from side to side or rotated.

(Step U7) Pixel Number Maximum?

The pixels are moved in step U6, and determination is made whether the pixel number of the blood cell included in the area becomes maximum. Specifically, while moving portions of the blood cell in the image with the edges enhanced in step T1, checking is made of the number of pixels in locations where the moved portions of the blood cell overlap the groove area in the design information. When it is maximum, the area having a pixel position where the number of pixels is maximum is regard as the right groove area, and the extraction of flow path positions by the flow path position extracting unit 36 consisting of the series of steps U1-U7 is ended. When it is not maximum, with a determination that there is an error, the operation returns to step U6. Until the number of pixels of the blood cell becomes maximum, or noting a plurality of movement candidates with more pixel numbers than a predetermined value, from which a candidate with a maximum is extracted, steps U6 and U7 are repeated.

Thus, by executing steps U1-U7, the flow path position extracting unit 36 adjusts the pixel positions of the image with the edges enhanced by the Sobel filter 35a based on the design information on the grooves 26 and disk 24. Returning to the flow chart of FIG. 8, description will be made further.

(Step T3) Sobel Filter

The downstream Sobel filter 35b carries out the Sobel filter process in order to enhance, as edges, the shading differences of the image in the pixel positions adjusted by the flow path position extracting unit 36. The specific Sobel filter process will not be described since it is carried out using the foregoing equation (1) and equation (2) as described for the upstream Sobel filter 35a also.

The image of the disk 24 with enhanced edges after the Sobel filter process by the Sobel filter 35b is as shown in FIG. 12. Although it is in black-and-white reversal in practice, for expediency of illustration, FIG. 12 shows it schematically in black-and-white reversal.

(Step T4) Straight Line Drawing

The straight line drawing unit 37, as shown in FIG. 13, draws a plurality of straight lines parallel to the grooves 26 (draws straight line group Lp in FIG. 13) on the image with the edges enhanced by the Sobel filter 35b in step T3. Since the grooves 26 are formed to extend radially of the disk 24 in this embodiment, each straight line group Lp consisting of a plurality of straight lines is drawn along radial directions. A profile based on the straight line groups Lp is as shown in FIG. 14. The horizontal axis of the profile represents the length of the radius, and "0" represents the center of the disk 24.

(Step T5) Boundary Calculation

The boundary calculating unit 38 obtains boundaries between the plasma and blood cell resulting from the plasma separation, based on the profile (see FIG. 14) of the plurality of straight lines drawn by the straight line drawing unit 37 in step T4. In FIG. 14, the area on the horizontal axis from "0" to a peak position appearing adjacent the middle is an area of air, the area from the peak position appearing adjacent the middle to a peak position appearing outward is an area of plasma, and the area further outward of the peak position appearing outward is an area of blood cell. Since the profile relates to the straight line group Lp consisting of a plurality of straight lines, the peak positions corresponding to the boundaries also appear in a plurality of locations. Therefore, by obtaining averages of these peak positions, boundaries between air and plasma are obtained, and boundaries between plasma and blood cell are also obtained.

Thus, by executing steps T1-T5, the Sobel filter 35a, flow path position extracting unit 36, Sobel filter 35b, straight line drawing unit 37, and boundary calculating unit 38 carry out image processing based on the shading differences of the image in the grooves 26 of the disk 24 picked up by the image pickup unit 34. Returning to the flow chart of FIG. 7, description will be made further.

(Step S8) Superimposition Process

The superimposition processing unit 39, based on the image picked up by the image pickup unit 34 in step S6 and processed by the image processes in step S7, and the count information on $\beta^+$ rays provided by the imaging plate IP and reading unit 31, carries out a superimposition process for superimposing the image processed by the image processes and the distribution image of the count information on $\beta^+$ rays in order to obtain count information on $\beta^+$ rays per unit volume. Specifically, the superimposition process is carried out to move the plasma and blood cell areas up and down and from side to side, and determine, as a superimposing position, a position where the overlap with the count information (IP image) of $\beta^+$ rays provided by the imaging plate IP and reading unit 31 becomes maximum, as in step U7. And volumes of the plasma and blood cell divided by the boundary calculating unit 38 in step T5, respectively, are obtained, and count information of $\beta^+$ rays in each of the plasma and blood cell in the distribution image superimposed on the plasma and blood cell is obtained. By dividing the count information on $\beta^+$ rays in each area of the plasma and blood cell by the volume, a radioactive concentration which is the count information on $\beta^+$ rays per unit volume is determined for each of the plasma and blood cell.

When an attempt is made to determine separating locations of the liquid (blood in this embodiment) based only on shading differences of the image, there is a problem that the boundaries of the separated liquid (boundaries between plasma and blood cell or between air and plasma in this embodiment) cannot be extracted accurately since the shading differences are not uniform. Further, in this embodiment, plasma, because it is clear and colorless, cannot be discriminated from the areas of air only by the shading differences of the image. With the measuring system in this embodiment, the boundary calculating device (boundary calculating unit 38 in this embodiment) is provided for determining boundaries of the liquid (boundaries between plasma and blood cell or between air and plasma) picked up by the image pickup device (image pickup unit 34 in this embodiment). With such boundary calculating device (boundary calculating unit 38) provided, the boundaries of the separated liquid (boundaries between plasma and blood cell or between air and plasma) can be determined, and areas of the separated liquid (areas of air, plasma, and blood cell) can be determined accurately.

In this embodiment, the separating device, preferably, is a flat plate (disk 24 in this embodiment) grooved in a predetermined size. That is, since it is grooved in a predetermined size, if the boundary calculating device (boundary calculating unit 38 in this embodiment) determines boundaries of the liquid (boundaries between plasma and blood cell or between air and plasma) fed into the flat plate (disk 24), the area of the grooves 26 or the volume of the grooves 26 divided and grooved in the predetermined size can be specified.

In this embodiment, the flat plate is a planar disk 24, which is grooved in the predetermined size radially of the disk 24 as shown in FIG. 4. The rotating device (motor 28 in this embodiment) is disposed centrally of the disk 24 for rotating the disk 24, and the liquid to be measured (blood in this embodiment) is centrifuged using the centrifugal force of the disk 24 generated by the rotating device (motor 28). Further, in this embodiment, the liquid to be measured is blood, and plasma separation is carried out to centrifuge the blood into plasma and blood cell using the centrifugal force of the flat plate (disk 24) generated by the rotating device (motor 28).

Further, in this embodiment, the boundary calculating device (boundary calculating unit 38) determines the boundaries based on the shading differences (differences in absorbance in this embodiment) of the image of the separated liquid (blood in this embodiment) in the separating device (disk 24 in this embodiment) picked up by the image pickup device (image pickup unit 34 in this embodiment). When the boundary calculating device (boundary calculating unit 38) determines the boundaries using such shading differences of the image, this embodiment performs the following process.

This embodiment includes the edge enhancing device (upstream Sobel filter 35*a* in this embodiment) for enhancing, as edges, the shading differences of the image of the separated liquid in the separating device (disk 24 in this embodiment) picked up by the image pickup device (image pickup unit 34 in this embodiment). The boundary calculating device (boundary calculating unit 38) determines the boundaries based on the image with the edges enhanced by the edge enhancing device (Sobel filter 35*a*). In this case, since the image with the edges enhanced by the edge enhancing device (Sobel filter 35*a*) is used, the boundaries can be determined easily and accurately.

In this embodiment, the separating device (disk 24 in this embodiment) is the flat plate (disk 24 in this embodiment) grooved in a predetermined size, and the edge enhancing device (upstream Sobel filter 35*a* in this embodiment) is provided for enhancing, as edges, the shading differences of the image of the separated liquid in the separating device (disk 24 in this embodiment) picked up by the image pickup device (image pickup unit 34 in this embodiment). The boundary calculating device (boundary calculating unit 38) determines the boundaries based on the image with the edges enhanced by the edge enhancing device (Sobel filter 35*a*). Thus, even though the separating device is the flat plate (disk 24) in this embodiment, since the image with the edges enhanced by the edge enhancing device (Sobel filter 35*a*) is used, the boundaries can be determined easily and accurately.

Where the separating device is limited to the flat plate (disk 24 in this embodiment), the measuring system further includes a flow path position extracting device (flow path position extracting unit 36 in this embodiment). This flow path position extracting device (flow path position extracting unit 36), based on the design information on the grooves 26 having the predetermined size on the flat plate (disk 24), and the flat plate (disk 24), extracts flow path positions of the grooves 26 by adjusting pixel positions of the grooves 26 in the image with the edges enhanced by the edge enhancing device (upstream Sobel filter 35*a* in this embodiment). Further, the boundary calculating device (boundary calculating unit 38 in this embodiment) determines the boundaries based on the image in pixel positions adjusted by the flow path position extracting device (flow path position extracting unit 36). In this case, with the flat plate (disk 24) grooved in the predetermined size, the design information of the grooves 26 and the flat plate (disk 24) is known beforehand, and in other words, the flat plate (disk 24) has been grooved in the predetermined size based on this design information. By adjusting the pixel positions of the shading differences of the image using this design information, errors can be reduced to determine the boundaries with increased accuracy. Where only the above edge enhancing device (Sobel filter 35*a*) is provided and the flow path position extracting device (flow path position extracting unit 36) is not provided, not only the grooves 26 (flow paths) but all that is included in the flat plate (disk 24) is edge-enhanced by the edge enhancing device (Sobel filter 35*a*). Therefore, edges of areas (areas of plasma and blood cell in this embodiment) of the liquid (blood in this embodiment) to be divided are not fully enhanced. So, the flow path position extracting device (flow path position extracting unit 36) extracts the flow path positions of the grooves 26 by adjusting the pixel positions, to fully enhance the edges of the areas (areas of plasma and blood cell) of the liquid (blood) to be divided, to facilitate determination of the boundaries. When the flow path position extracting device (flow path position extracting unit 36) adjusts the pixel positions using such design information, this embodiment performs the following process.

This embodiment additionally includes an edge enhancing device (downstream Sobel filter 35*b* in this embodiment) for enhancing, as edges, the shading differences of the image in the pixel positions adjusted by the flow path position extracting device (flow path position extracting unit 36 in this embodiment). The boundary calculating device (boundary calculating unit 38 in this invention) determines as boundaries the edges enhanced by the edge enhancing device (Sobel filter 35*b*). In this case, since the edges enhanced by the edge enhancing device (Sobel filter 35*b*) are determined as boundaries, the boundaries can be determined easily with increased accuracy.

This embodiment includes a straight line drawing device (straight line drawing unit 37 in this embodiment) for drawing a plurality of straight lines parallel to the grooves 26 on the image with the edges enhanced by the edge enhancing device (downstream Sobel filter 35*b* in this embodiment) which enhances, as the edges, the shading differences of the image in the pixel positions adjusted by the flow path position extracting device (flow path position extracting unit 36 in this embodiment). The boundary calculation device (boundary calculating unit 38 in this embodiment) determines the boundaries based on a profile of the plurality of straight lines drawn by the straight line drawing device (straight line drawing unit 37).

Where, as in this embodiment, the edge enhancing device (downstream Sobel filter 35*b* in this embodiment) is provided for enhancing, as edges, the shading differences of the image in the pixel positions adjusted by the flow path position extracting device (flow path position extracting unit 36 in this embodiment), the edge enhancing device (Sobel filter 35b) acts as a second edge enhancing device. And, further, the edge enhancing device (upstream Sobel filter 35a in this embodiment) for enhancing, as edges, the shading differences of the image of the separated liquid (blood in this embodiment) in the flat plate (disk 24 in this embodiment) picked up by the image pickup device (image pickup unit 34 in this embodiment) acts as a first edge enhancing device (upstream Sobel filter 35a). This first edge enhancing device (Sobel filter 35a) is an upstream edge enhancing device (Sobel filter 35a) for enhancing, as edges, the shading differences of the image of the separated liquid (blood) in the flat plate (disk 24) picked up by the image pickup device (image pickup unit 34). The second edge enhancing device (Sobel filter 35b) is a downstream edge enhancing device (Sobel filter 35b) for enhancing, as edges, the shading differences of the image in the pixel positions adjusted by the flow path position extracting device (flow path position extracting unit 36). Thus, the second edge enhancing device (Sobel filter 35b) carries out edge enhancement after edge enhancement by the above first edge enhancing device (Sobel filter 35a). The boundary can be determined easily by carrying out the edge enhancement twice.

In this embodiment, the edge enhancing device carries out the edge enhancement by primary differential which determines differences between an attention pixel (central pixel $p_{22}$ in this embodiment) and its peripheral pixels (peripheral pixels $p_{11}$, $p_{12}$, $p_{13}$, $p_{21}$, $p_{23}$, $p_{31}$, $p_{32}$ and $p_{33}$ in this embodiment). As the edge enhancement by primary differential, this embodiment employs a Sobel filter.

Further, this embodiment includes a detecting device (imaging plate IP and reading unit 31 in this embodiment) for simultaneously and two-dimensionally detecting radiation included in the liquid to be measured (blood in this embodiment) to obtain two-dimensional image information of the radiation, and includes a superimposition processing device (superimposition processing unit 39 in this embodiment) for carrying out a superimposition process to superimpose the image of the separated liquid (blood) in the separating device (disk 24 in this embodiment) picked up by the image pickup device (image pickup unit 34 in this embodiment) and a distribution image of the two-dimensional image information obtained by the detecting device (imaging plate IP and reading unit 31). Based on areas of the liquid (blood) (areas of air, plasma, and blood cell in this embodiment) divided by the boundary calculating device (boundary calculating unit 38 in this embodiment), and areas (areas of air, plasma, and blood cell) in the distribution image superimposed thereon, information on the radiation (count information of $\beta^+$ rays) in these areas is obtained. With such superimposition process carried out, information on the radiation in these areas can be obtained accurately.

Where the above superimposition processing device (superimposition processing unit 39 in this embodiment) is provided, and where the liquid to be measured is blood including radiation, the following determination is made. The separating device (disk 24 in this embodiment) carries out plasma separation which centrifuges and separates the blood into plasma and blood cell, and the boundary calculating device (boundary calculating unit 38 in this embodiment) determines boundaries between plasma and blood cell. The detecting device (imaging plate IP and reading unit 31 in this embodiment) simultaneously and two-dimensionally detects the radiation included in the blood to obtain two-dimensional image information of the radiation. The superimposition processing device (superimposition processing unit 39) carries out a superimposition process to superimpose the image resulting from the plasma separation and the distribution image of the two-dimensional image information obtained by the detecting device (imaging plate IP and reading unit 31). Based on the plasma and blood cell divided by the boundary calculating device (boundary calculating unit 38) and the plasma and blood cell in the distribution image superimposed thereon, a radioactive concentration is determined for each of the plasma and blood cell.

This invention is not limited to the foregoing embodiment, but may be modified as follows:

(1) The foregoing embodiment has been described taking blood as an example of the liquid to be measured in the measuring system. The liquid to be measured is not limited to blood, but may be a liquid including a radioactive material or a fluorescent agent, or a mixed liquid used in an analyzing apparatus, for example. When the liquid to be measured is a liquid including a fluorescent substance, the detecting device (imaging plate IP and reading unit 31 in the embodiment) may simultaneously and two-dimensionally detect light included in the liquid to obtain two-dimensional image information of the light. Based on areas of the liquid divided by the boundary calculating device (boundary calculating unit 38 in the embodiment) and areas in the distribution image superimposed thereon, densities of the fluorescent substance in these areas may be determined.

(2) In the foregoing embodiment, the separating device has been the flat plate (disk 24 in the embodiment) grooved in a predetermined size. However, the flat plate is not limitative as long as it has a construction for separating the liquid to be measured (blood in the embodiment).

(3) The foregoing embodiment provides the disk 24 and the rotating device (motor 28 in the embodiment) for application to the centrifugal separation of the liquid (blood in the embodiment) in liquid collection (blood collection in the embodiment). Where centrifugal separation is not carried out, it is not absolutely necessary to provide the disk 24 and the rotating device. The flat plate may be a rectangular plate, a polygonal plate or the like, without being limited to the disk 24 but, preferably, is shaped to have a rotation center at the center of gravity, considering that it is rotated.

(4) The foregoing embodiment provides a plurality of grooves 26 formed radially by grooving radially of the disk 24, but it is not absolutely necessary to arrange them radially. They may be arranged parallel to one another, for example.

(5) The foregoing embodiment, for the boundary calculating device (boundary calculating unit 38 in the embodiment) to determine boundaries, includes, as arranged upstream thereof, the edge enhancing devices (Sobel filters 35a, 35b in the embodiment), the flow path position extracting device (path position extracting unit 36 in the embodiment), and the straight line drawing device (straight line drawing unit 37 in the embodiment). It is not absolutely necessary to provide all of them.

(6) The foregoing embodiment has been described taking, as an example of the edge enhancing device, the Sobel filter for carrying out edge enhancement by primary differential which determines differences between an attention pixel and its peripheral pixels. This is not limitative but may be a device usually used for carrying out edge enhancement. For example, instead of being limited to the edge enhancement by primary differential, this may be a Laplacian filter for edge enhancement by quadratic differential which determines further differences of the differences between the attention pixel and its peripheral pixels, or instead of being limited to the Sobel filter for edge enhancement by primary differential, may be a Prewitt filter. Thus, a device usually used for edge enhancement will serve the purpose, instead of being limited to the edge enhancement by primary differential or quadratic differential.

(7) The foregoing embodiment provides the detecting device (imaging plate IP and reading unit 31 in the embodiment) for simultaneously and two-dimensionally detecting light or radiation to obtain two-dimensional image information of the light or radiation, and the superimposition processing device (superimposition processing unit 39 in the embodiment). However, it is not absolutely necessary to provide the detecting device or the superimposition processing device. While the image pickup device has been described taking an optical image pickup device like the flat head scanner for example, this may be a radiation image pickup device formed of a radiation emitting device and a radiation detecting device. With the radiation image pickup device, varied portions of a centrifuged liquid have different radioactive concentrations, and these differences are used.

(8) In the foregoing embodiment, the detecting device (imaging plate IP and reading unit 31 in the embodiment) carries out simultaneous detection (coincidence counting) of the radiation included in the liquid to be measured (blood in the embodiment). As noted in modification (1) above, this may be a liquid including a fluorescent agent. In the case of a liquid including a fluorescent agent, for example, a fluorescent substance which is the fluorescent agent will be included in the liquid, and the measuring apparatus will measure light generated from the fluorescent substance with a CCD camera or the like to obtain information on the light per unit volume accurately. Instead of the imaging plate IP and reading unit 31, two-dimensional radiation sensors (scintillator arrays, photomultipliers, or semiconductor detectors) may be used. Light generated from a luminescent substance may be measured similarly.

(9) The foregoing embodiment has been described taking, for example, automatic blood collection by the blood collecting apparatus 10 in the measuring system. The liquid collecting method is not limited to the automatic liquid collecting apparatus. A method may be employed, in which the liquid is caused to drip to the grooves 26 of the disk 24 by the operator's manual work.

INDUSTRIAL UTILITY

As described above, this invention is suitable for a measuring system which measures light generated from a luminescent or fluorescent substance included in a liquid to be measured, or radiation included in the liquid to be measured.

The invention claimed is:

1. A measuring system for measuring light generated from a luminescent or fluorescent substance included in a liquid to be measured, or radiation included in the liquid to be measured, comprising:
    a separating device for separating the liquid to be measured;
    an imager forming an image of the separated liquid; and
    a boundary calculating device for determining boundaries of the separated liquid in the image, wherein:
    the measuring system measures the light or the radiation from the separated liquid within the determined boundaries, respectively;
    the separating device is a flat plate having grooves of a predetermined size, the liquid being in one of the grooves in which the liquid is separated;
    an edge enhancing device is provided for enhancing shading differences in the image of the separated liquid in the flat plate, the shading differences being treated as edges;
    a flow path position extracting device is provided for extracting, based on design information on the grooves having the predetermined size in the flat plate, and the flat plate, positions of the grooves by adjusting positions of pixels of the edges in the image; and
    the boundary calculating device determines the boundaries based on the pixels of the edges in the image comprising a detecting device for simultaneously and two-dimensionally detecting the light or radiation included in the liquid to be measured to obtain two-dimensional image information of the light or radiation, and a superimposition processing device for carrying out a superimposition process to superimpose the image of the separated liquid in the separating device picked up by the image pickup device and a distribution image of the two-dimensional image information obtained by the detecting device, wherein, based on areas of the liquid divided by the boundary calculating device, and areas in the distribution image superimposed thereon, information on the light or radiation in these areas is obtained; wherein the liquid to be measured is blood including radiation, the separating device carries out plasma separation which centrifuges and separates the blood into plasma and blood cell, and the boundary calculating device determines boundaries between plasma and blood cell, the detecting device simultaneously and two-dimensionally detects the radiation included in the blood to obtain two-dimensional image information of the radiation, the superimposition processing device carries out a superimposition process to superimpose the image resulting from the plasma separation and the distribution image of the two-dimensional image information obtained by the detecting device, and based on the plasma and blood cell divided by the boundary calculating device and the plasma and blood cell in the distribution image superimposed thereon, a radioactive concentration is determined for each of the plasma and blood cell.

2. The measuring system according to claim 1, wherein the flat plate is a planar disk, and grooves are formed in the predetermined size radially of the disk.

3. The measuring system according to claim 2, comprising a rotating device disposed centrally of the disk for rotating the disk, the liquid to be measured being centrifuged using a centrifugal force of the disk generated by the rotating device.

4. The measuring system according to claim 3, wherein the liquid to be measured is blood, and plasma separation is carried out to centrifuge the blood and separate the blood into plasma and blood cell using the centrifugal force of the flat plate generated by the rotating device.

5. The measuring system according to claim 1, further comprising an edge enhancing device for enhancing, as edges, the shading differences of the image in the pixel positions adjusted by the flow path position extracting device, wherein the boundary calculating device determines as boundaries the edges enhanced by the edge enhancing device.

6. The measuring system according to claim 5, comprising a straight line drawing device for drawing a plurality of straight lines parallel to the grooves on the image with the edges enhanced by the edge enhancing device which enhances, as the edges, the shading differences of the image in the pixel positions adjusted by the flow path position extracting device, wherein the boundary calculating device determines the boundaries based on a profile of the plurality of straight lines drawn by the straight line drawing device.

7. The measuring system according to claim 5, wherein the edge enhancing device which enhances, as the edges, the shading differences of the image in the pixel positions adjusted by the flow path position extracting device is a second edge enhancing device, and further the edge enhancing device which enhances, as the edges, the shading differences in the image of the separated liquid in the flat plate picked up by the image pickup device is a first edge enhancing device, the second edge enhancing device carrying out edge enhancement after edge enhancement by the first edge enhancing device.

8. The measuring system according claim 1, wherein the edge enhancing device carries out the edge enhancement by primary differential which determines differences between an attention pixel and its peripheral pixels.

9. The measuring system according to claim 1, wherein the edge enhancing device carries out the edge enhancement by quadratic differential which determines further differences of differences between the attention pixel and its peripheral pixels.

10. The measuring system according to claim 1, wherein the liquid to be measured is a liquid including a fluorescent substance, the detecting device simultaneously and two-dimensionally detects light included in the liquid to obtain two-dimensional image information of the light, and based on areas of the liquid divided by the boundary calculating device and areas in the distribution image superimposed thereon, densities of the fluorescent substance in these areas are determined.

* * * * *